(12) United States Patent
Plumptre et al.

(10) Patent No.: US 10,376,645 B2
(45) Date of Patent: Aug. 13, 2019

(54) DRIVE MECHANISM FOR A DRUG DELIVERY DEVICE

(71) Applicant: SANOFI-AVENTIS DEUTSCHLAND GMBH, Frankfurt am Main (DE)

(72) Inventors: David Aubrey Plumptre, Worcestershire (GB); Naceur Rekaya, Warwickshire (GB); Paul Richard Draper, Worcestershire (GB); Paul Griffin, Worcestershire (GB); David Richard Mercer, Dorset (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 444 days.

(21) Appl. No.: 14/770,848

(22) PCT Filed: Mar. 10, 2014

(86) PCT No.: PCT/EP2014/054532
§ 371 (c)(1),
(2) Date: Aug. 27, 2015

(87) PCT Pub. No.: WO2014/139920
PCT Pub. Date: Sep. 18, 2014

(65) Prior Publication Data
US 2016/0008548 A1 Jan. 14, 2016

(30) Foreign Application Priority Data
Mar. 13, 2013 (EP) .................................... 13159054

(51) Int. Cl.
*A61M 5/31* (2006.01)
*A61M 5/315* (2006.01)

(52) U.S. Cl.
CPC ...... *A61M 5/3146* (2013.01); *A61M 5/31571* (2013.01); *A61M 5/31515* (2013.01);
(Continued)

(58) Field of Classification Search
CPC .......... A61M 5/31515; A61M 5/31585; A61M 5/3146
See application file for complete search history.

(56) References Cited

U.S. PATENT DOCUMENTS

| 533,575 A | 2/1895 | Wilkens |
| 5,226,895 A | 7/1993 | Harris |

(Continued)

FOREIGN PATENT DOCUMENTS

| CN | 102076372 A | 5/2011 |
| EP | 0937471 | 8/1999 |

(Continued)

OTHER PUBLICATIONS

Chinese Office Action for CN Application No. 201480013757.2, dated Aug. 2, 2017.
(Continued)

*Primary Examiner* — William R Carpenter
(74) *Attorney, Agent, or Firm* — Fish & Richardson P.C.

(57) ABSTRACT

The present disclosure concerns a drive mechanism for a drug delivery device, having a first and a second state and comprising a piston rod configured to be moved in a distal direction when the drive mechanism is operated and an adjusting member, wherein the adjusting member is rotatable relative to a body of the drug delivery device in the first state of the drive mechanism and is prevented from rotating relative to the body in the second state of the drive mechanism, and wherein the adjusting member is configured to adjust an axial position of the piston rod in the first state of the drive mechanism.

13 Claims, 17 Drawing Sheets

(52) U.S. Cl.
CPC ..... *A61M 5/31551* (2013.01); *A61M 5/31585* (2013.01); *A61M 2207/00* (2013.01); *A61M 2207/10* (2013.01)

(56) References Cited

U.S. PATENT DOCUMENTS

| | | | |
|---|---|---|---|
| 5,279,586 | A | 1/1994 | Balkwill |
| 5,304,152 | A | 4/1994 | Sams |
| 5,320,609 | A | 6/1994 | Haber et al. |
| 5,383,865 | A * | 1/1995 | Michel ............... A61M 5/31553 604/186 |
| 5,480,387 | A * | 1/1996 | Gabriel ................ A61M 5/20 604/134 |
| 5,505,704 | A | 4/1996 | Pawelka et al. |
| 5,582,598 | A | 12/1996 | Chanoch |
| 5,626,566 | A | 5/1997 | Petersen et al. |
| 5,674,204 | A | 10/1997 | Chanoch |
| 5,688,251 | A | 11/1997 | Chanoch |
| 5,921,966 | A * | 7/1999 | Bendek ................ A61M 5/24 604/207 |
| 5,961,495 | A | 10/1999 | Walters et al. |
| 6,004,297 | A | 12/1999 | Steenfeldt-Jensen et al. |
| 6,193,698 | B1 | 2/2001 | Kirchhofer et al. |
| 6,221,046 | B1 | 4/2001 | Burroughs et al. |
| 6,235,004 | B1 | 5/2001 | Steenfeldt-Jensen et al. |
| 6,248,095 | B1 | 6/2001 | Giambattista et al. |
| 6,899,698 | B2 | 5/2005 | Sams |
| 6,936,032 | B1 | 8/2005 | Bush, Jr. et al. |
| 7,241,278 | B2 * | 7/2007 | Moller ................. A61M 5/24 604/211 |
| 2002/0052578 | A1 | 5/2002 | Moller |
| 2002/0120235 | A1 | 8/2002 | Enggaard |
| 2003/0050609 | A1 | 3/2003 | Sams |
| 2004/0059299 | A1 | 3/2004 | Moller |
| 2004/0210199 | A1 * | 10/2004 | Atterbury ......... A61M 5/31535 604/224 |
| 2004/0267207 | A1 | 12/2004 | Veasey et al. |
| 2005/0113765 | A1 | 5/2005 | Veasey et al. |
| 2005/0261634 | A1 * | 11/2005 | Karlsson ................ A61M 5/20 604/197 |
| 2006/0153693 | A1 | 7/2006 | Fiechter et al. |
| 2007/0142789 | A1 | 6/2007 | Fisher et al. |
| 2008/0208144 | A1 * | 8/2008 | Moller .............. A61M 5/31548 604/220 |
| 2009/0275914 | A1 | 11/2009 | Harms et al. |
| 2009/0275916 | A1 | 11/2009 | Harms et al. |
| 2012/0283657 | A1 * | 11/2012 | Kouyoumjian ......... A61M 5/24 604/211 |
| 2012/0283659 | A1 * | 11/2012 | Kouyoumjian ... A61M 5/31551 604/211 |

FOREIGN PATENT DOCUMENTS

| | | |
|---|---|---|
| EP | 0937476 | 8/1999 |
| JP | 2012-525172 A | 10/2012 |
| WO | 99/38554 | 8/1999 |
| WO | 01/10484 | 2/2001 |
| WO | 2007/017051 A1 | 2/2007 |
| WO | 2009/132777 A1 | 11/2009 |
| WO | 2010/124961 A1 | 11/2010 |
| WO | 2011/039215 | 4/2011 |
| WO | 2011/039229 | 4/2011 |

OTHER PUBLICATIONS

Chinese Search Report for CN Application No. 201480013757.2, dated Jul. 24, 2017.

International Search Report for Int. App. No. PCT/EP2014/054532, completed Apr. 29, 2014.

Japanese Office Action for JP Application No. 2015-562062, dated Jan. 17, 2018.

* cited by examiner

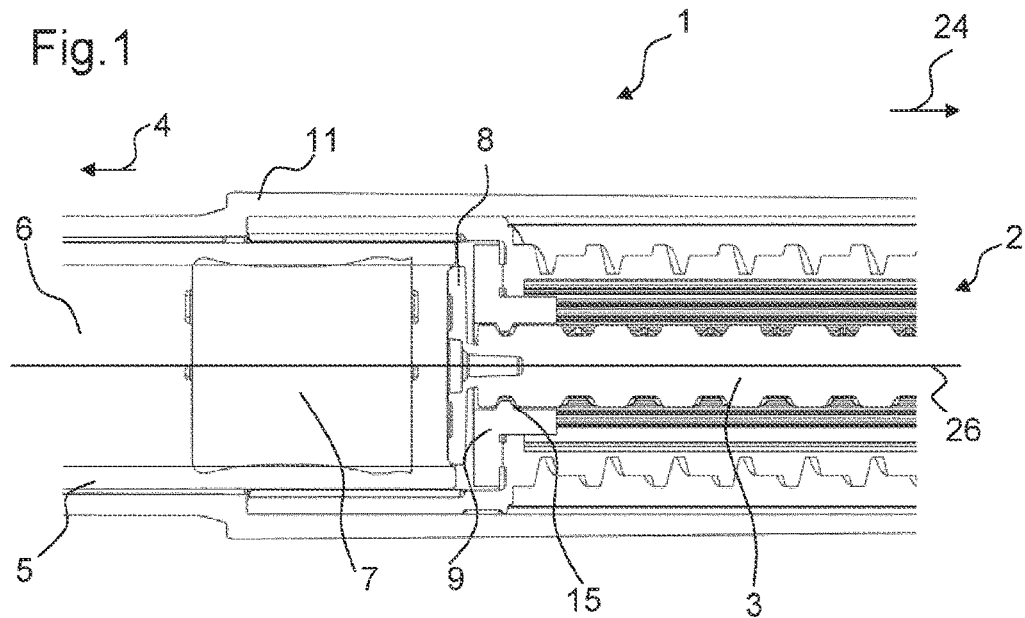
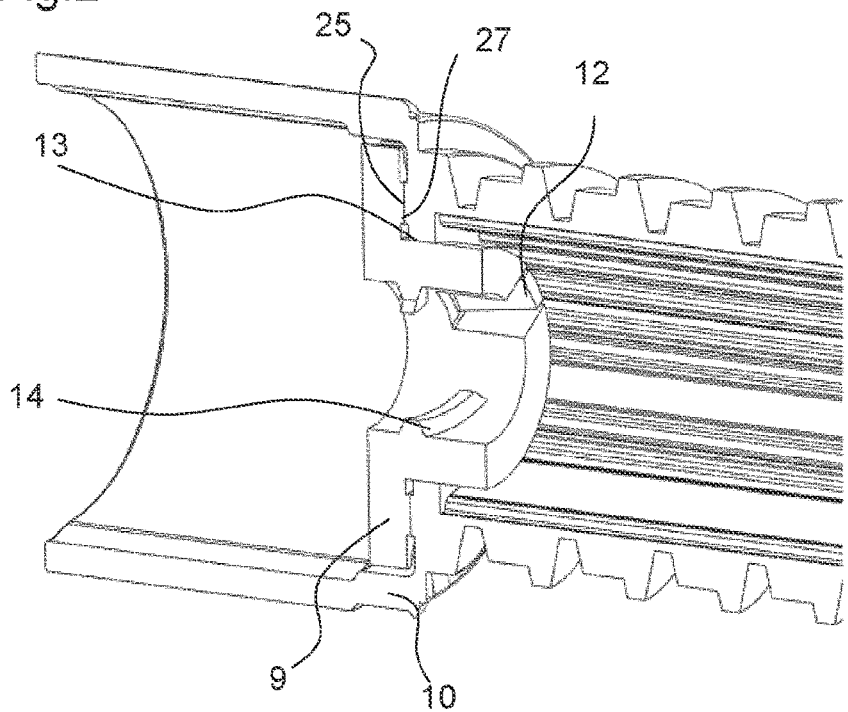

DRIVE MECHANISM FOR A DRUG DELIVERY DEVICE

CROSS REFERENCE TO RELATED APPLICATIONS

The present application is a U.S. National Phase Application pursuant to 35 U.S.C. § 371 of International Application No. PCT/EP2014/054532 filed Mar. 10, 2014, which claims priority to European Patent Application No. 13159054.9 filed Mar. 13, 2013. The entire disclosure contents of these applications are herewith incorporated by reference into the present application.

TECHNICAL FIELD

The present invention relates to a drive mechanism for a drug delivery device.

BACKGROUND

Drug delivery devices are generally known for the administration of a medicinal product, for example insulin or heparin, but also for other medicinal products, in particular for self-administration by a patient. A drug delivery device may be configured as a pen-type injector which may dispense a pre-set dose of a fluid medicinal product. However, the drug delivery device may also deliver a variable dose of the medicinal product.

Before the first use of the drug delivery device, the user may have to dispense a small amount of the product. Thereby, the effect of manufacturing tolerances of the mechanical components of the drug delivery device may be eliminated. The operation of dispensing a small amount of a product before the first use is also referred to as a priming operation of the drug delivery device. Users who are unfamiliar with the drug delivery device may fail to or incorrectly prime their drug delivery device before dispensing the first dose. Another disadvantage of a drug delivery device requiring a priming operation is that a user might accidently inject a priming dose. Moreover, priming operations result in a waste of the medicinal product as the medicinal product expelled during the priming operation cannot be used to treat the patient.

SUMMARY

It is an object of the present disclosure to provide a drive mechanism for use in a drug delivery device which helps to improve usability and ensures the accuracy of the first administered dose of a medicinal product.

This object is solved by the drive mechanism according to present claim 1.

According to a first aspect of the present disclosure, a drive mechanism for a drug delivery device is provided. The drive mechanism has a first and a second state and comprises a piston rod configured to be moved in a distal direction when the drive mechanism is operated and an adjusting member, wherein the adjusting member is rotatable relative to a body of the drug delivery device in the first state of the drive mechanism and is prevented from rotating relative to the body in the second state of the drive mechanism and wherein the adjusting member is configured to adjust an axial position of the piston rod in the first state of the drive mechanism.

The terms "distal" and "proximal" shall be defined as follows. In an assembled drug delivery device, the distal end of the drive mechanism is defined as the end which is closest to a dispensing end of the drug delivery device. In an assembled drug delivery device, the proximal end of the drive mechanism is defined as the end which is furthest away from the dispensing end of the drug delivery device. Moreover, a distal direction is defined as a direction towards the distal end and a proximal direction is defined as a direction towards the proximal end.

The drive mechanism may be a mechanism that allows to set a dose and to dispense a dose of a medicinal product. The drive mechanism may comprise the piston rod, the elements that are configured to move the piston rod and elements that are configured to constrain a movement of the piston rod. The drive mechanism may include all elements that are required to carry out the dose setting and/or dose dispensing operation.

The first state of the drive mechanism may be a pre-assembled state. In the first state, the drive mechanism may be assembled to a cartridge holder holding a cartridge. However, in the first state, mechanical tolerances between the drive mechanism and the cartridge holder and mechanical tolerances between the elements of the drive mechanism may be present. In the first state, due to manufacturing tolerances or other mechanical tolerances, the drive mechanism may be not correctly aligned to other elements of the drug delivery device. In particular, the distance between elements of the drive mechanism, for example between the piston rod and a bung of the cartridge, may not be well-defined. Due to mechanical tolerances and other tolerances in the manufacturing process, this distance may vary from one drug delivery device to another in the first state of the drive mechanism.

Moreover, other elements of the drug delivery device, e.g. a button, may not have been assembled to the drug delivery device in the first state of the drive mechanism.

In the first state, the drive mechanism may be usable for preparative purposes only and may not be suited for a dose setting operation or a dose dispense operation.

The first state may be defined as a state wherein the adjusting member is rotatable relative to a body of the drug delivery device.

The second state of the drive mechanism may be defined as a state wherein the adjusting member is prevented from rotating relative to the body.

The drive mechanism being in its first state may be transferred to its second state by rotationally locking the adjusting member relative to the body. Further, the drive mechanism being in its second state may be transferred to its first state by releasing the engagement between the adjusting member and the body such that the adjusting member is permitted to rotate relative to the body. In some embodiments, the engagement may only be released if one of the adjusting member and the body is damaged during the release.

In the second state of the drive mechanism, the adjusting member may be engaged to the body such that the adjusting member is permitted to rotate relative to the body and such that the engagement of the adjusting member with the body may only be released by damaging at least one of the elements of the drive mechanism or of the drug delivery device. In alternate embodiments, the adjusting member may be releasably engaged to the body in the second state of the drive mechanism. Accordingly, in these embodiments, the engagement of the adjusting member with the body may be released without damaging one of the elements of the drive mechanism or of the drug delivery device.

In the second state of the drive mechanism, the tolerances may have been eliminated. In the second state of the drive mechanism, the drug delivery device may be used by a patient for the application of a medicinal product. Accordingly, the drive mechanism may be ready to carry out a dose setting and a dose dispensing operation in the second state. In particular, when the drive mechanism is operated for the first time in its second state, the drive mechanism can be used without the requirement of a priming step to prepare for the first dose delivery.

The piston rod may be configured to be moved in a distal direction when the drive mechanism is operated in the second state of the drive mechanism. The operation of the drive mechanism may be a dose dispense operation.

The piston rod may also be configured to be moved in a distal direction when the drive mechanism is operated in the first state of the drive mechanism. In this case, the operation of the drive mechanism may be a priming operation.

The adjusting member may comprise a nut. The adjusting member may be threadedly engaged with the piston rod. The adjusting member may constrain a movement of the piston rod in the second state of the drive mechanism. In particular, the adjusting member may constrain a movement of the piston rod in the second state of the drive mechanism such that the piston rod is permitted only to carry out a concurrent axial and rotational movement relative to the adjusting member. As the adjusting member is prevented from rotating relative to the body in the second state of the drive mechanism, the adjusting member may constrain a movement of the piston rod in the second state of the drive mechanism such that the piston rod is permitted only to carry out a concurrent axial and rotational movement relative to the body.

Further, the adjusting member may be engaged with the piston rod in the first state of the drive mechanism as well. In particular, the adjusting member may be threadedly engaged with the piston rod in the first state of the drive mechanism. However, as the adjusting member is permitted to rotate relative to the body in the first state of the drive mechanism, the adjusting member may not constrain a movement of the piston rod relative to the body in the first state of the drive mechanism. Instead, the piston rod may be permitted to be moved axially relative to the body without rotating relative to the body, in the first state of the drive mechanism.

In particular, the adjusting member may be configured to be rotated relative to the body in the first state of the drive mechanism. Thereby, the adjusting member may move the piston rod axially relative to the body such that the axial position of the piston rod may be adjusted in this manner.

Further, the adjusting member may be configured such that a rotation of an external member is converted into a rotation of the adjusting member.

The external member may not be a part of the drive mechanism. Instead, the external member may be a part of an external assembly machine that is configured to engage with the adjusting member in the first state of the drive mechanism and that is removed from the drug delivery device in the second state of the drive mechanism. Accordingly, the adjusting member may be configured to be engaged with the external member in the first state of the drive mechanism.

The adjusting member may comprise a controlling feature that is suitable for being engaged with the external member. The controlling feature may be integrally formed with the adjusting member. The controlling feature may comprise teeth arranged at a periphery of the adjusting member. In particular, the periphery of the adjusting member may be formed as a toothed gear which is configured to be engaged with the external member.

The external member may also comprise a toothed gear. The external member may be driven, in particular rotated, by a drive mechanism of the external assembly machine. The external member may rotate the adjusting member such that the adjusting member moves the piston rod in the distal direction towards the bung of the cartridge.

Further, the drive mechanism may comprise a rotation preventing member wherein the rotation preventing member is configured to be engaged with the adjusting member in the second state of the drive mechanism thereby preventing a rotation of the adjusting member relative to the body.

In particular, the rotation preventing member may be configured to be engaged with the controlling feature of the adjusting member in the second state of the drive mechanism. Accordingly, the controlling feature may fulfill two purposes in the drive mechanism. The controlling feature may be configured such that a rotation of the external member is transferred to a rotation of the adjusting member, thereby moving the piston rod in the distal direction, when the controlling feature is engaged with the external member. Further, the controlling feature may be configured such that a further rotation of the adjusting member relative to the body is prevented when the controlling feature is engaged with the rotation preventing member.

Alternatively, the rotation preventing member may be configured to engage with another element of the adjusting member.

The engagement of the rotation preventing member with the adjusting member in the second state may provide further advantages. The rotation preventing member may close an opening in the body and in a housing of the drug delivery device when engaged with the adjusting member. Thereby, the rotation preventing member may provide for a smooth surface of the drug delivery device. The rotation preventing member may prevent the interior of the drug delivery device from being polluted in the second state of the drive mechanism as the rotation preventing member closes the interior of the drug delivery device and thereby forms an encapsulation of the interior.

Further, the adjusting member may comprise a first contact surface and, in the second state of the drive mechanism, the first contact surface may abut the body, thereby preventing the adjusting member from rotating relative to the body. In particular, the body may comprise a second contact surface. In the second state of the drive mechanism, the first contact surface may abut the second contact surface.

A rotation of the adjusting member relative to the body may be prevented by a frictional engagement of the first contact surface with the body. Accordingly, the adjusting member may be self-locking. The frictional engagement may be generated by an axial load transmitted to the adjusting member by the piston rod resulting in friction between the first and the second contact surface.

In particular, the first contact surface of the adjusting member and the corresponding second contact surface of the body may comprise faces which are arranged in an angle non-perpendicular to a longitudinal axis of the drive mechanism. When these faces abut each other, an increased frictional engagement occurs which prevents rotation of the adjusting member relative to the body.

Alternatively, the frictional engagement between the first contact surface of the adjusting member and the body may not be sufficiently strong to prevent a rotation between the adjusting member and the body. In this case, the frictional engagement impedes a rotation of the adjusting member relative to the body. Accordingly, due to the frictional engagement, the torque required to rotate the adjusting member relative to the body may be increased.

Additionally or alternatively, the first contact surface may comprise locking features that are configured to engage with the body when the contact surface abuts the body in the second state of the drive mechanism, thereby preventing the adjusting member from rotating relative to the body.

The locking features may comprise ramp features arranged on the first and the second contact surface. The locking features may be configured such that they allow a rotation of the adjusting member relative to the body when the adjusting member has a small amount of axial play relative to the body. Further, the locking features may be configured to prevent a rotation of the adjusting member relative to the body when the small amount of play is eliminated. Accordingly, in the first state of the drive mechanism, the locking features may not prevent a rotation of the adjusting member relative to the body. In the second state of the drive mechanism, the axial play between the adjusting member and the body may be eliminated, e.g. by a rotation preventing member being engaged to the adjusting member, thereby the locking features prevent any further rotation of the adjusting member relative to the body.

Further, in the second state of the drive mechanism, a force may be exerted in a proximal direction onto the adjusting member thereby bringing the first contact surface in abutment with the body. The force in the proximal direction may be exerted by the piston rod. The force may be generated by an abutment of the piston rod with the bung, resulting in a tension of a system comprising the piston rod and the adjusting member.

Additionally or alternatively, an adhesive may prevent the adjusting member from rotating relative to the body in the second state of the drive mechanism. The adhesive may be arranged on the first contact surface and/or the second contact surface. Accordingly, when the contact surface abuts the second contact surface, the adhesive couples the first and the second contact surface with each other. Further, the adhesive may be additionally activated using ultra-violet light, ultrasonically or by using radio frequency energy.

Additionally or alternatively, the adjusting member may be welded to the body in the second state of the drive mechanism.

Each of welding and adhesive coupling provides a strong joint between the adjusting member and the body. In particular, welding and adhesive coupling allow providing an adjusting member which does not comprise teeth. Accordingly, the adjusting member can be coupled with the body by the adhesive or by the welding in any rotational position relative to the body. In particular, the adjusting member does not have to be moved in one of a number discrete rotational positions relative to the body defined by teeth. Accordingly, these embodiments allow for a high resolution in the angular position of the adjusting member. Accordingly, as the adjusting member can be oriented in one of an unlimited number of rotational positions relative to the body, the axial load applied by the piston rod to the bung can be set very precisely.

Further, the adjusting member may comprise a fixing feature. The fixing feature may be either configured to engage with the body of the drug delivery device such that the adjusting member is moveable in an axial direction relative to the body only by a small predetermined distance or the fixing feature may be configured to engage with the body of the drug delivery device such that the adjusting member is prevented from moving in an axial direction relative to the body.

In particular, the fixing feature may allow the adjusting member to move relative to the body only by a small predetermined distance in the first state of the drive mechanism. In the second state of the drive mechanism, the fixing feature may cooperate with the rotation preventing member such that the adjusting member is prevented from moving axially relative to the body. In particular, the rotation preventing member may eliminate the axial play such that no axial play between the adjusting member and the body is present in the second state of the drive mechanism.

The fixing feature may be configured to engage with the body by a snap-fit connection. The body may comprise a protrusion that is configured such that the fixing feature may be snap fitted to the protrusion. The protrusion of the body may be rotationally symmetric thereby permitting the adjusting member to rotate relative to the body.

Further, the present disclosure concerns a drug delivery device comprising the drive mechanism and the body wherein the drive mechanism is arranged at least partially inside the body.

In particular, the drive mechanism may be the drive mechanism disclosed above such that every structural and functional feature disclosed with respect to that drive mechanism may also be present in the drug delivery device.

The body may comprise a first engagement feature that is configured to engage the adjusting member in the second state of the drive mechanism, thereby preventing a rotation of the adjusting member relative to the body in the second state of the drive mechanism.

The first engagement feature may be arranged at an inner surface of the body. The first engagement feature may comprise a locking arm. The first engagement feature may comprise teeth.

Further, the adjusting member may comprise a second engagement feature wherein the first engagement feature of the body may be configured to engage with the second engagement feature of the adjusting member in the second state of the drive mechanism.

The second engagement feature may comprise teeth arranged at the periphery of the adjusting member. In particular, the teeth of the first engagement feature may be configured to engage with the teeth of the second engagement feature in the second state of the drive mechanism.

Alternatively, the second engagement feature may comprise a fragile surface that is configured to be crushed when the first engagement feature of the body engages with the second engagement feature. The fragile surface may be formed by a thin material. The fragile surface may form a ring. The fragile surface provides the advantage that it allows the first and the second engagement feature to engage with each other not only in a limited number of discrete positions but in any rotational position relative to each other. Thus, the position of the adjusting member may be chosen very precisely without being restricted to one of a number of discrete positions such that the axial load applied to the bung by the piston rod may be set very precisely.

Further, the drug delivery device may comprises a housing, wherein the body is arranged inside the housing, wherein the body has a first and a second rotational position relative to the housing, and wherein the first engagement feature of the body is engaged with the adjusting member when the body is in its second rotational position.

Accordingly, the body may be rotatable relative to the housing.

In particular, the housing may comprise a non-circular inner diameter. Ramp features may be arranged at the inner surface of the housing. The body may also comprise a non-circular outer diameter. The first rotational position of the body relative to the housing is configured such that the first engagement feature of the body is arranged in a distance relative to the second engagement feature of the adjusting member. The second rotational position may be configured such that the first engagement feature is engaged with the second engagement feature. In particular, during the rotation of the body relative to the housing, the ramp features of the housing may move the first engagement feature into engagement with the second engagement feature.

Further, the body may comprise an opening arranged at a periphery of the body, wherein an external member and/or a rotation-preventing member of the drive mechanism are each moveable at least partially through the opening into the body, thereby engaging with the adjusting member.

The opening may form a slot. The opening may be closed by a rotation preventing member or by another member in the second state of the drive mechanism.

Another aspect of the present disclosure concerns a method of assembling the drive mechanism. The method comprises the steps of:
 providing the drive mechanism in its first state,
 rotating the adjusting member relative to the body of the drug delivery device, thereby adjusting the axial position of the piston rod, and
 rotationally locking the adjusting member to the body such that the adjusting member is prevented from rotating relative to the body, thereby transferring the drive mechanism to its second state.

In particular, the drive mechanism may be the drive mechanism disclosed above such that every structural and functional feature disclosed with respect to that drive mechanism may also be present in the method.

The term "medicinal product", as used herein, preferably means a pharmaceutical formulation containing at least one pharmaceutically active compound,
 wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound,
 wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis,
 wherein in a further embodiment the pharmaceutically active compound comprises at least one peptide for the treatment and/or prophylaxis of diabetes mellitus or complications associated with diabetes mellitus such as diabetic retinopathy,
 wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(w-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2) 25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, β, ε, δ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

In the following, the disclosed devices and methods are described in further detail with reference to the drawings, wherein

BRIEF DESCRIPTION OF THE FIGURES

FIG. 1 shows a part of a drug delivery device in a cross-sectional view,

FIG. 2 shows an adjusting member being engaged with a body,

DETAILED DESCRIPTION

Figure 3:
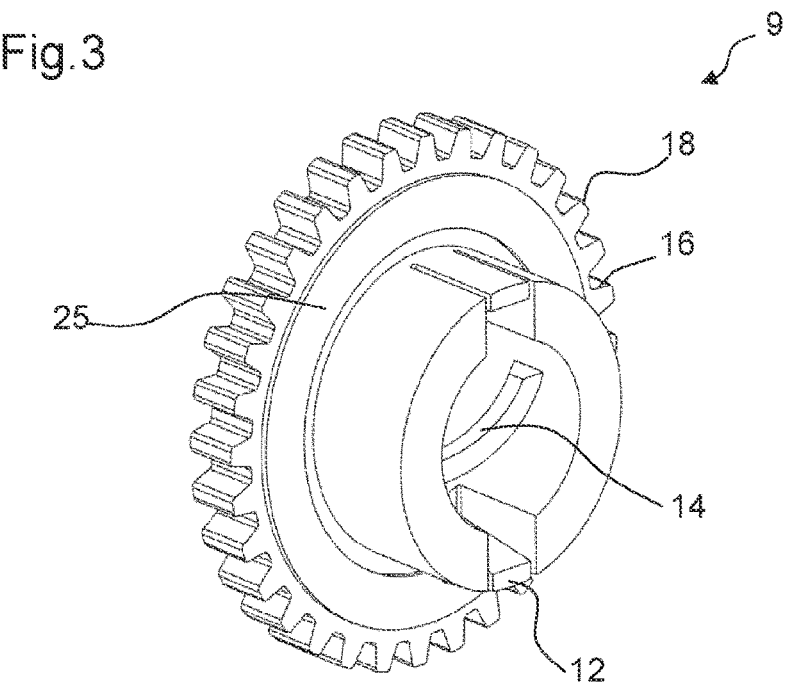
FIG. 3 shows the adjusting member shown in FIG. 2 in a perspective view.

FIG. 1 shows a part of a drug delivery device 1 in a cross-sectional view. The drug delivery device 1 shown in FIG. 1 is an injection device. In particular, the drug delivery device 1 is a pen-type injection device. Moreover, the drug delivery device 1 is a fixed dose device. The drug delivery device 1 is a disposable device.

The drug delivery device 1 comprises a drive mechanism 2. The drive mechanism 2 comprises a piston rod 3. The piston rod 3 is movable in the distal direction 4. In particular, the piston rod 3 is configured to be moved in the distal direction 4 in a dose dispense operation.

Further, the drug delivery device 1 comprises a cartridge holder 5. A cartridge 6 comprising a bung 7 is arranged in the cartridge holder 5. By a movement of the bung 7 in a distal direction 4 towards an outlet of the cartridge 6, a medicinal product may be expelled from the cartridge 6.

Moreover, the drug delivery device comprises a body 10. In particular, the body 10 is an inner body. Further, the drug delivery device comprises a housing 11. The body 10 is arranged inside the housing 11. The body 10 is fixed to the housing 11 such that it cannot move relative to the housing 11. Further, the cartridge holder 5 comprising the cartridge 6 is fixed to the body 10. The drive mechanism 2 is arranged at least partially inside the body 10.

The drive mechanism 2 has a first state and a second state. In the first state, the distance between the piston rod 3 and the bung 7 is not well-defined. For example, manufacturing tolerances and other mechanical tolerances may be present in the first state. Accordingly, the distance between the bung 7 and the distal end of the piston rod 3 may vary from one drug delivery device 1 to another in the first state. FIG. 1 shows the drive mechanism 2 in its first state.

As will be discussed later, in the second state of the drive mechanism 2, the distance between the bung 7 and the piston rod 3 is well-defined. In particular, the piston rod 3 may abut the bung 7 in the second state of the drive mechanism 2.

The piston rod 3 comprises a bearing 8. The bearing 8 is arranged at the distal end of the piston rod 3. The bearing 8 is integrally formed with the piston rod 3. Alternatively, the bearing 8 may be snap-fitted to a main body of the piston rod 3. The bearing 8 is configured to exert a force on the bung 7 when the piston rod 3 is moved in the distal direction.

Moreover, the drive mechanism 2 comprises a drive member (not shown in FIG. 1) which is configured to control a movement of the piston rod 3. The drive member may comprise a drive sleeve (not shown in FIG. 1).

Further, the drive mechanism 2 comprises an adjusting member 9. In the first state of the drive mechanism 2, the adjusting member 9 is rotatable relative the body 10 of the drug delivery device 1. In the first state, a rotational movement of the adjusting member 9 may adjust the axial position of the piston rod 3 relative to the adjusting member 9 and, thereby, relative to the body 10. However, in the second state of the drive mechanism 2, the adjusting member 9 is prevented from the rotating relative to the body 10. In the second state of the drive mechanism 2, the adjusting member 9 constrains a movement of the piston rod 3 relative to the body 10.

FIG. 2 shows the adjusting member 9 being engaged with the body 10. FIG. 3 shows the adjusting member 9 in a perspective view.

The adjusting member 9 comprises a nut.

The adjusting member 9 is engaged to the body 10 in the first and in the second state of the drive mechanism 2. The adjusting member 9 comprises a fixing feature 12 that is engaged with the body 10 of the drug delivery device 1 in the first and in the second state of the drive mechanism 2. The fixing feature 12 is configured such that the adjusting member 9 is either not movable axially relative to the body 10 or that the adjusting member 9 is moveable only by a small predetermined distance when the adjusting member 9 is engaged to the body 10.

The fixing feature 12 is configured to be snap-fitted to the body. The body 10 comprises a corresponding protrusion 13 such that the fixing feature 12 is configured to be snap-fitted to the protrusion 13. The protrusion 13 is formed as a rotary bearing.

The fixing feature 12 is configured such that the adjusting member 9 has a small amount of play for an axial movement when engaged with the body 10. This small amount corresponds to the small predetermined distance by which the adjusting member 9 is movable relative to the body 10. In an alternate embodiment, the fixing feature 12 is configured such that the adjusting member 12 is not movable relative to the body 10 in an axial direction. In this case, the snap-fit connection is configured without play.

In the first state of the drive mechanism 2, the adjusting member 9 is enabled to rotate freely relative to the body 10. In particular, the fixing feature 12 of the adjusting member 9 and the protrusion 13 of the body 10 being engaged with each other do not prevent a rotation of the adjusting member 9 relative to the body 10.

The piston rod 3 is configured to be moved relative to the adjusting member 9 only in a concurrent rotational and axial movement in the first and in the second state of the drive mechanism 2. For this purpose, the adjusting member 9 comprises a helical thread 14 arranged at its inner surface. The helical thread 14 is a part-thread comprising only parts of a helical thread. Further, the piston rod 3 comprises a thread 15 arranged at its outer surface. The helical thread 14 of the adjusting member 9 is engaged with the thread 15 of the piston rod 3 in the first and the second state of the drive mechanism 2.

Accordingly, the adjusting member 9 and the piston rod 3 are threadedly engaged. Therefore, by rotating the adjusting member 9, e.g. during an assembly of the drive mechanism 2, the piston rod 3 is driven axially in a distal direction 4. In particular, the adjusting member 9 is rotated during the assembly process of the drive mechanism 2 until the piston rod 3 is moved in the distal direction 4 so far that the piston rod 3 abuts the bung 7. Thereby, the drive mechanism 2 is transferred to its second state. The distance between the piston rod 3 and the bung 7 is now precisely determined, i.e. the distance equals zero.

Figure 4:
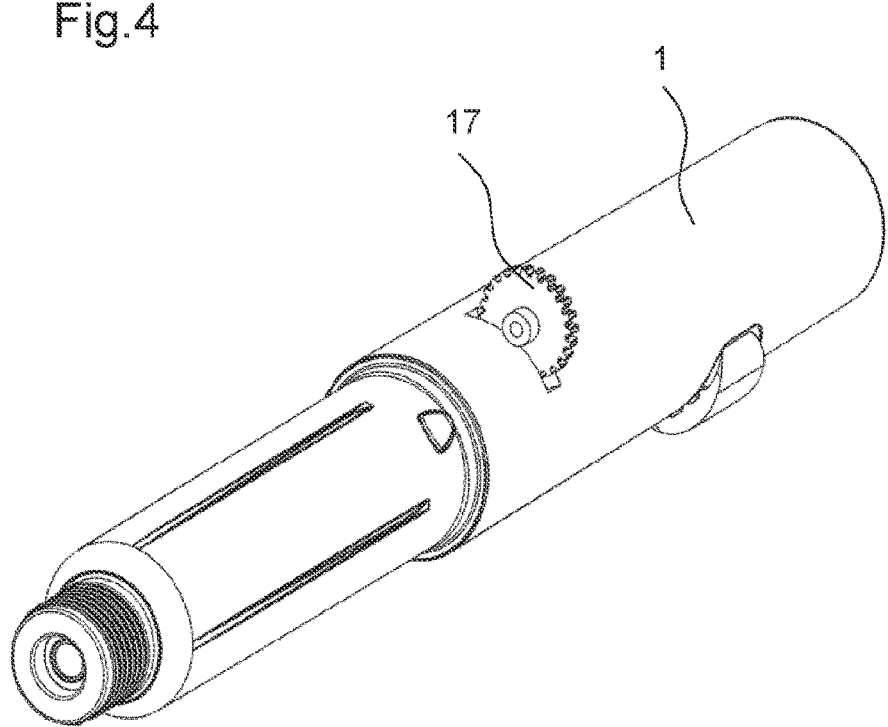
FIG. 4 shows an engagement of an external member with the drug delivery device shown in FIG. 1.

FIG. 4 shows an engagement of an external member 17 with the adjusting member 9.

The adjusting member 9 further comprises a controlling feature 16. The controlling feature 16 is configured to engage with the external member 17 in the first state of the drive mechanism 2. For example, the external member 17 is an external driving gear which may be part of an assembly machine.

The controlling feature 16 is configured to transfer a rotation of the external member 17 into a rotation of the adjusting member 9 relative to the body 10 in the first state of the drive mechanism 2. In particular, the controlling feature 16 comprises teeth 18 arranged at a periphery of the adjusting member 9. In particular, the outer circumference of the adjusting member 9 is formed as a toothed gear.

Figure 5:
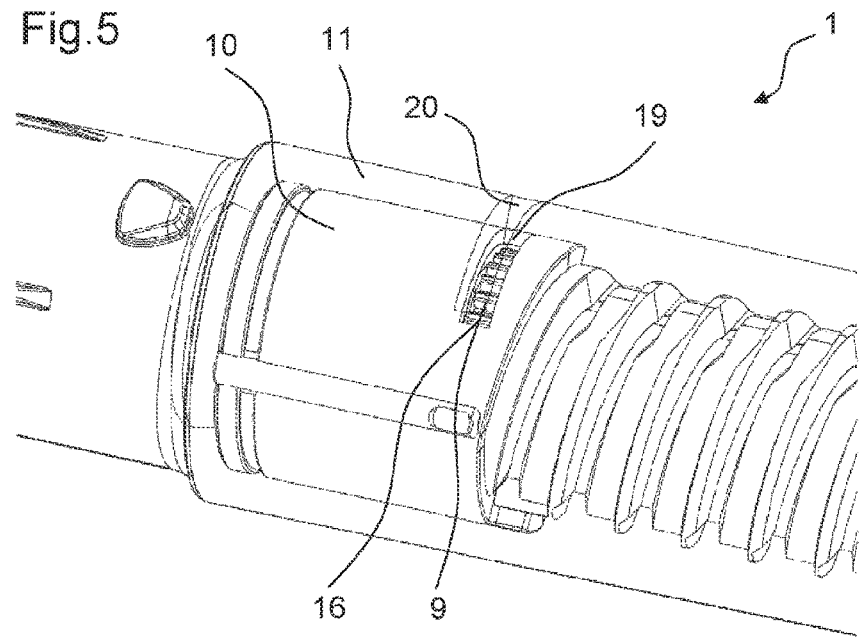
FIG. 5 shows a part of the drug delivery device shown in FIG. 1 in a perspective view with some of the elements of the drug delivery device shown partially transparent.

FIG. 5 shows a part of the drug delivery device 1 in a perspective view with some of the elements of the drug delivery device 1 shown partially transparent. The body 10 comprises an opening 19 that is arranged at the periphery of the body 10. The opening 19 is formed such that the external member 17 is movable partially through the opening 19 into the body 10 such that the external member 17 can engage with the controlling feature 16 of the adjusting member 9. The opening 19 formed in the body 10 comprises a slot. Further, a similar opening 20 is formed in the housing 11 of the drug delivery device 1. In the first state of the drive mechanism 2, the openings 19, 20 of the body 10 and of the housing 11 are arranged such that they overlap each other.

Figure 6:
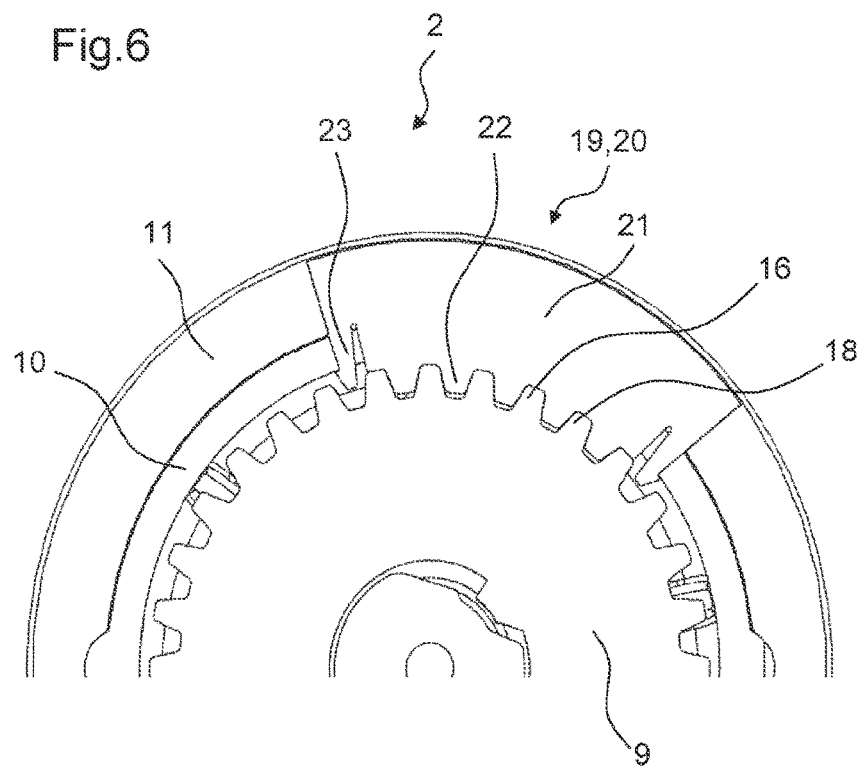
FIG. 6 shows a cross-sectional view of a drive mechanism in its second state.

FIG. 6 shows a cross-sectional view of the drive mechanism 2 in its second state. The drive mechanism 2 further comprises a rotation preventing member 21. In the first state of the drive mechanism 2, the rotation preventing member 21 is not engaged with other elements of the drive mechanism 2. In the second state of the drive mechanism 2, the rotation preventing member 21 is engaged with the adjusting member 9. In particular, the rotation preventing member 21 is engaged with the controlling feature 16 of the adjusting member 9. The rotation preventing member 21 comprises teeth 22 that engage with the teeth 18 of the controlling feature 16. Due to this engagement, a further rotation of the adjusting member 9 relative to the body 10 is prevented.

Further, the rotation preventing member 21 engages with the body 10 of the drug delivery device 1. This engagement may be a snap-fit engagement. The rotation preventing member 21 comprises snap-fit features 23 that engage with the opening 19 defined in the body 10. The snap-fit features 23 which interact with the body 10 are configured such that the rotation preventing member 21 cannot be removed from the body 10 once it is inserted into the opening 19 without damaging the drug delivery device 1.

Once the rotation preventing member 21 is engaged with the body 10, the rotation preventing member 21 cannot be moved relative to the body 10. As the rotation preventing member 21 is simultaneously engaged with the controlling feature 16, the adjusting member 9 can also not be moved relative to the body 10.

The adjusting member 9 must rest in one of a number of discrete positions defined by the meshing of the teeth 18 of the controlling feature 16 with the teeth 22 of the rotation preventing member 21. Accordingly, there is a maximum accuracy that can be achieved with this method, defined by the number of teeth 18 of the controlling feature 16.

In the following, the assembly process of the drug delivery device 1 is discussed. In the first state of the drive mechanism 2, the adjusting member 9 is engaged to the body 10 by an engagement of the fixing feature 12 to the body 10 such that the adjusting member 9 is axially constrained and free to rotate relative to the body 10. The body 10, the drive member, the piston rod 3 and the cartridge holder 5 are already fully assembled in the first state of the drive mechanism 2. The first state of the drive mechanism 2 may be defined as a state wherein the adjusting member 9 is rotatable relative to the body 10 of the drug delivery device 1. Further, in the first state, the distal end of the piston rod 3 is arranged at a not well-defined distance to the bung 7 of the cartridge 6. This distance may vary from one drug delivery device 1 to another.

Then, the external member 17 is inserted into the openings 19, 20 of the housing 11 and the body 10. The external member 17 engages with the controlling feature 16 of the adjusting member 9. The external member 17 is driven rotationally, e.g. by an external motor. The external motor is provided with some means for detecting the driving torque being transmitted, e.g. a torque cell and some means for detecting how far it has rotated, e.g. a rotary encoder. Alternatively, the external motor may comprise a slip clutch that is designed to slip once a preset torque has been reached.

The external member 17 being rotated by the external motor causes the adjusting member 9 to rotate. The direction of rotation is chosen such that the piston rod 3 is forced to advance axially in the distal direction 4 towards the bung 7 by the threaded engagement of the piston rod 3 and the adjusting member 9. As soon as the bearing 8 of the piston rod 3 contacts the bung 7, an axial load is generated in the piston rod 3 which exerts a force on the adjusting member 9 in the proximal direction 24. This force moves the adjusting member 9 in the proximal direction 24 into contact with the body 10.

In particular, the adjusting member 9 comprises a first contact surface 25. The first contact surface 25 is a flat surface that is perpendicular to a longitudinal axis 26 of the drive mechanism 2. Further, the body 10 also comprises a second contact surface 27 being perpendicular to the longitudinal axis 26 of the drive mechanism 2. When the adjusting member 9 is moved in the proximal direction 24 into contact with the body 10, the first contact surface 25 of the adjusting member 9 abuts the second contact surface 27 of the body 10. This abutment causes a friction which impedes a further rotation of the adjusting member 9 relative to the body 10, thereby increasing the torque required to rotate the adjusting member 9 relative to the body 10.

The external motor continues to rotate until the torque reaches a predetermined level which indicates that the desired compressive load has been applied to bung 7. Accordingly, the external member 17 can now be removed. If a clutch is used, the external member 17 is simply withdrawn once the clutch begins to slip.

As the desired compressive load is now applied to the bung 7 by the bearing 8 of the piston rod 3, the priming process is complete. In particular, the distance between the piston rod 3 and the bung 7 is now well-defined.

At this point the rotation preventing member 21 is inserted into the opening 19 of the body 10. The rotation preventing member 21 engages with the body 10 and with the adjusting member 9, thereby preventing any further rotation of the adjusting member 9 relative to the body 10.

Accordingly, the drive mechanism 2 is now in its second state. The second state of the drive mechanism 2 is defined by the adjusting member 9 being prevented from rotating relative to the body 10. In the second state of the drive mechanism 2, the distance between the piston rod 3 and the bung 7 is well-defined.

Even if the axial load in the piston rod 3 reduces during storage or usage of the drug delivery device 1, the adjusting member 9 is now prevented from being rotated relative to the body 10 due to its engagement with the rotation preventing member 21.

Further, the outer surface of the rotation preventing member 21 is designed to sit flush with the housing 11. Accordingly, the rotation preventing member 21 closes the opening 20 of the housing 11 and forms a smooth surface of the housing 11.

Figure 7:
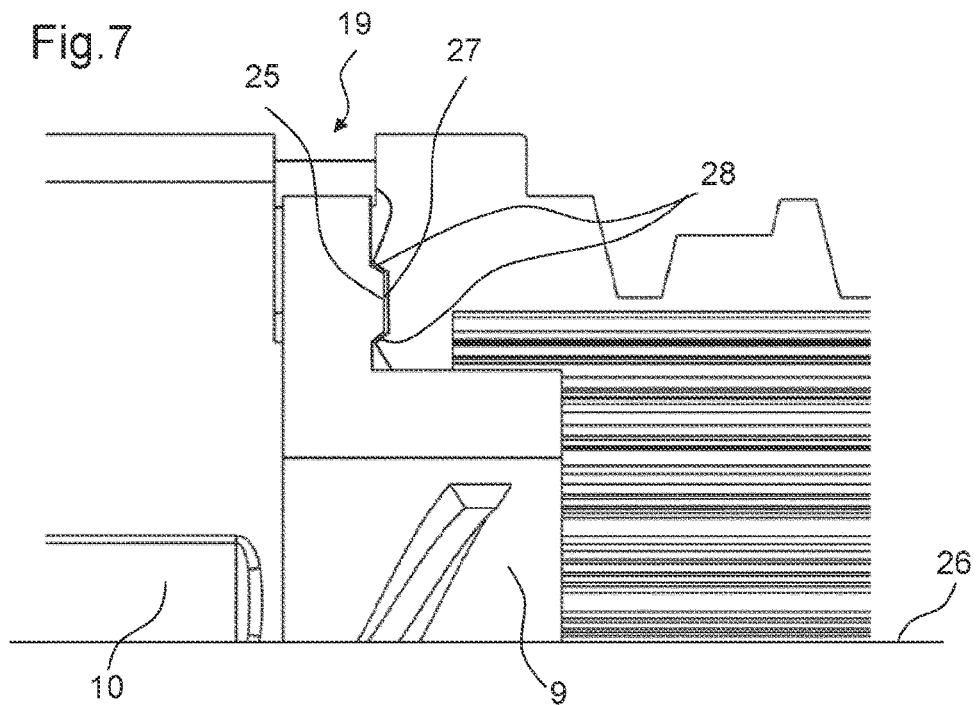
FIG. 7 shows the adjusting member being engaged with the body according to a second embodiment of the drive mechanism.

FIG. 7 shows the adjusting member 9 being engaged to the body 10 according to a second embodiment. According to the second embodiment, the adjusting member 9 also comprises the first contact surface 25 which abuts the corresponding second contact surface 27 of the body 10 in the second state of the drive mechanism 2. Thereby, a rotation of the adjusting member 9 relative to the body 10 is prevented.

In the second embodiment, the first contact surface 25 of the adjusting member 9 is shaped such that the friction of the frictional engagement is increased. Further, the second contact surface 27 of the body 10 is also shaped to increase the friction of the frictional engagement. In particular, during operation of the drug delivery device 1, a rotation of the adjusting member 9 relative to the body 10 is prevented due to a frictional engagement between the first and the second contact surface 25, 27.

In particular, the first contact surface 25 of the adjusting member 9 and the second contact surface 27 of the body 10 comprise faces 28 which are arranged relative to the longitudinal axis 26 of the drive mechanism 2 in a non-perpendicular angle. In particular, the first and the second contact surface 25, 27 comprise faces 28 which are arranged such that the surface normal of the faces 28 and the longitudinal axis 26 of the drive mechanism 2 form an angle in the range of 20° to 70°.

Accordingly, for a given axial load being transferred from the piston rod 3 to the adjusting member 9, the contact forces are increased compared to the contact forces which will occur between parallel contact surfaces.

In the embodiment shown in FIG. 7, each of the first and the second contact surface 25, 27 comprises two faces 28 arranged at a non-perpendicular angle relative to the longitudinal axis 26 of the drive mechanism 2. However, in alternate embodiments any number of non-perpendicular faces 28 may be present. The angle of the faces 28 is chosen to provide the best compromise between allowing the adjusting member 9 to rotate during the first state of the drive mechanism 2, but not in the second state of the drive mechanism 2.

Additionally, the rotation preventing member 21 may be inserted into the opening 19 of the body 10 in the second state of the drive mechanism 2. If the rotation preventing member 21 is inserted into the opening 19 of the body 10 in the second state of the drive mechanism 2 according to the second embodiment, the rotation preventing member 21 engages with the adjusting member 9. According to the second embodiment, the insertion of the rotation preventing member 21 is optional as a rotation of the adjusting member 9 relative to the body 10 is also prevented by the frictional engagement of the first contact surface 25 of the adjusting member 9 and the second contact surface 27 of the body 10. Accordingly, the rotation preventing member 21 may provide an additional prevention of the rotation of the adjusting member 9 relative to the body 10. Further, the rotation preventing member 21 closing the opening 20 of the housing 11 provides for a smooth outer surface of the drug delivery device 1.

Figure 8:
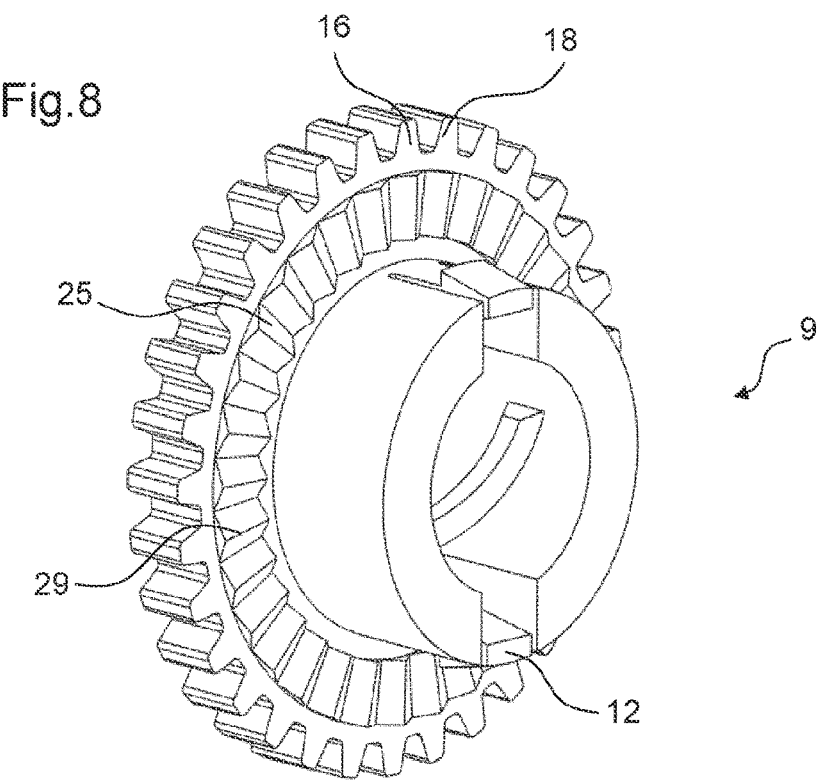
FIG. 8 shows the adjusting member according to a third embodiment of the drive mechanism.

FIG. 8 shows the adjusting member 9 according to a third embodiment. The adjusting member 9 is identical to the adjusting member 9 according to the first embodiment except that the first contact surface 25 of the adjusting member 9 comprises locking features 29. The locking features 29 are configured to engage with the body 10 when the first contact surface 25 abuts the body 10 in the second state of the drive mechanism 2. Thereby, the locking features 29 prevent the adjusting member 9 from rotating relative to the body 10.

The locking features 29 comprise ramp features. Further, the second contact surface 27 of the body 10 comprises corresponding locking features (not shown), e.g. identical ramp features. An engagement of the locking features 29 of the adjusting member 9 with the locking features of the body 10 results in rotationally locking the adjusting member 9 relative to the body 10.

The assembly of the drug delivery device 1 according to the third embodiment is similar to the assembly described with respect to the first embodiment. In the first state of the drive mechanism 2, the piston rod 3 is arranged at a not well-defined distance away from the bung 7 due to mechanical tolerances. Then the external member 17 engages with the adjusting member 9 and causes the adjusting member 9 to rotate relative to the body 10, thereby the piston rod 3 is forced to be moved concurrently rotational and axial in the distal direction 4 relative to the body 10.

As soon as the bearing 8 of the piston rod 3 contacts the bung 7, an axial load is generated by the piston rod 3 which will cause the adjusting member 9 to move into abutment with the body 10. This will cause the adjusting member 9 to alternately climb up and then drop down the ramp features of the body 10 as it is rotated. This is also the reason for the small amount of axial play allowed between the adjusting member 9 and the body 10 by the fixing feature 12 being engaged to the body 10. The external member 17 continues to rotate until the torque required to rotate the adjusting member 9 has reached a predetermined level indicating that the desired compressive load has been applied to the bung 7.

If a torque cell and an encoder are used, at this point the external member 17 will rotate to the nearest position at which the locking features 29 of the adjusting member 9 are fully interlocked with the locking features of the body 10. When the external member 17 is removed, the locking features 29 prevent any further rotation of the adjusting member 9 relative to the body 10. If a clutch is used instead, then the external member 17 is simply withdrawn once the clutch begins to slip, the axial load in the piston rod 3 will then force the adjusting member 9 to rotate slightly until the locking features 29 of the adjusting member 9 are fully engaged with the locking features of the body 10.

The size of the locking features 29 determines the angular resolution and hence the accuracy that is achievable with this embodiment.

The rotation preventing member 21 may additionally be used to provide an extra securing against a rotation of the adjusting member 9 and to provide for a smooth outer surface of the drug delivery device 1. The number of teeth 18 of the controlling feature 16 of the adjusting member 9 is related to the number of locking features 29 in such a way that the rotation preventing member 21 will always align correctly to the controlling feature 16 when the locking features 29 of the adjusting member 9 are fully interlocked with the locking features of the body 10. In this embodiment, the rotation preventing member 21 can additionally comprise a feature which prevents the adjusting member 9 from moving axially relative to the body 10 in the second state of the drive mechanism 2 by removing the axial play between the adjusting member 9 and to the body 10.

Figure 9:
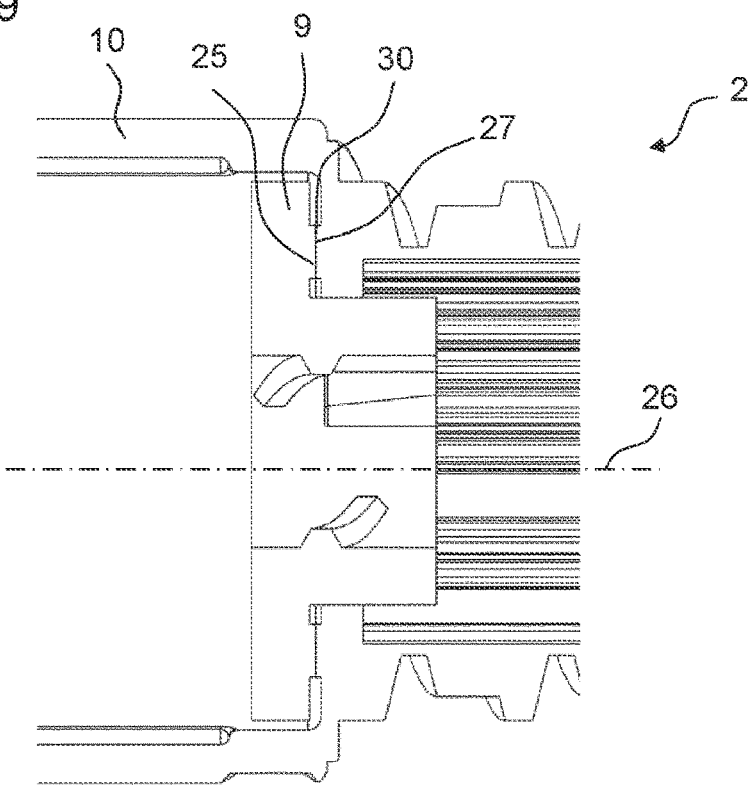
FIG. 9 shows the adjusting member being engaged with the body according to a fourth embodiment of the drive mechanism.

FIG. 9 shows the drive mechanism 2 according to a fourth embodiment. The first contact surface 25 of the adjusting member 9 is engaged to the second contact surface 27 of the body 10 by an adhesive 30 in the second state of the drive mechanism 2. Each of the first and the second contact surface 25, 27 is flat and arranged perpendicular to the longitudinal axis 26 of the drive mechanism 2. This results in the advantage of allowing a high resolution in the angular position of the adjusting member 9 relative to the body 10 which translates to a precise axial load on the bung 7.

Once the first contact surface 25 of the adjusting member 9 and the second contact surface 27 of the body 10 abut each other, they may be coupled by the adhesive 30. Additionally or alternatively, the adhesive 30 may be activated using ultraviolet light, ultrasonically or by using radio frequency energy.

The first and the second contact surface 25, 27 are designed to form a strong engagement without allowing excess adhesive to escape into other parts of the drive mechanism 2.

In this embodiment, the rotation prevention member 21 is not required to prevent a rotation of the adjusting member 9 relative to the body 10. Nevertheless, the rotation preventing member 21 may be used to provide additional rotation preventing security and to provide a smooth outer surface of the drug delivery device 1.

Figure 10:
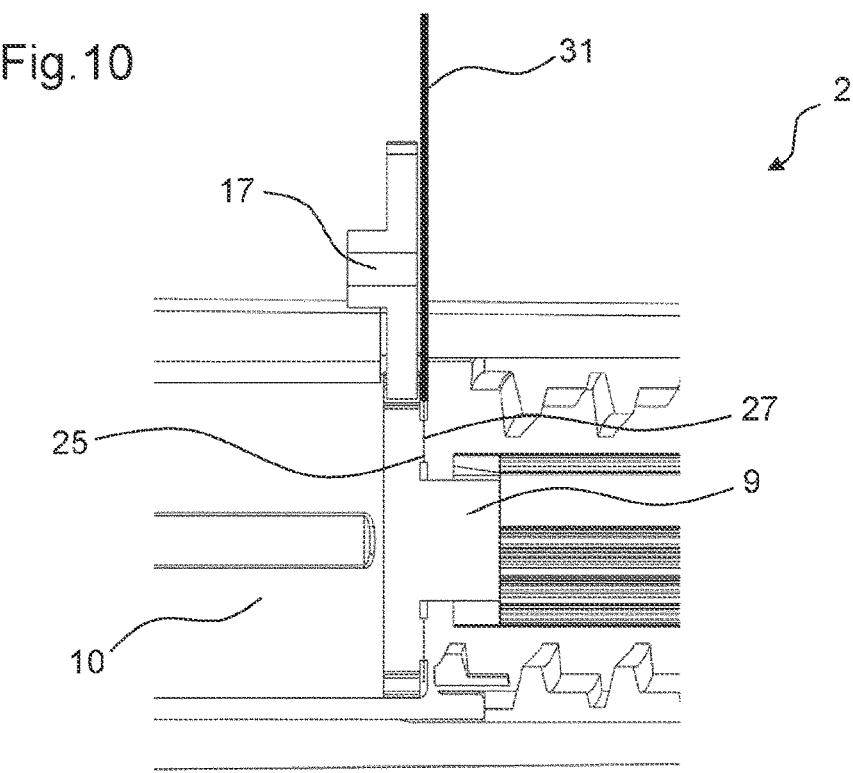
FIG. 10 shows the drive mechanism according to a fifth embodiment of the drive mechanism.

FIG. 10 shows the drive mechanism 2 according to a fifth embodiment.

In FIG. 10, the adjusting member 9 is welded to the body 10. Accordingly, in the second state of the drive mechanism 2, due to the welded engagement of the adjusting member 9 and the body 10, a rotation of the adjusting member 9 relative to the body 10 is prevented. During the assembly of the drug delivery device 1, the external member 17 engages the adjusting member 9 and rotates the adjusting member 9 until the torque required to rotate the external member 17 reaches a predetermined amount. Then, a laser beam 31 is directed to the first and the second contact surface 25, 27 of the adjusting member 9 and the body 10 with the external member 17 still engaged to the adjusting member 9. The laser beam 31 welds the first and the second contact surface 25, 27 together. Once the welded connection between the first and the second contact surface 25, 27 is cooled the external member 17 can be removed.

This embodiment also allows for flat contact surfaces 25, 27 of the adjusting member 9 and the body 10 resulting in allowing a high resolution in the angular position of the adjusting member 9 relative to the body 10 which translate to a precise axial load on the bung 7.

Again, a rotation preventing member 21 is optional, providing the advantage of an additional rotation preventing security and a smooth outer surface of the drug delivery device 1.

Figure 11:
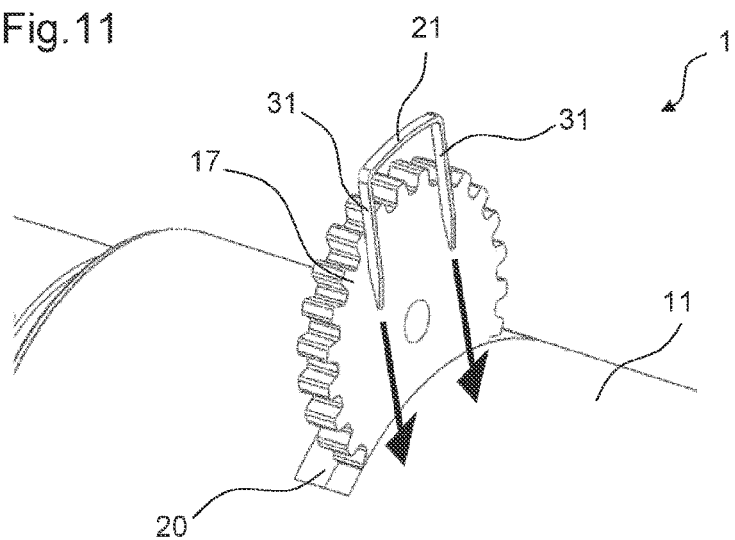
FIG. 11 shows a rotation preventing member approaching the drive mechanism according to a sixth embodiment of the drive mechanism in the first state of the drive mechanism.

FIG. 11 shows the drug delivery device 1 according to a sixth embodiment. According to this embodiment, the rotation preventing member 21 is used to prevent a rotation of the adjusting member 9 relative to the body 10 in the second state of the drive mechanism 2. In the sixth embodiment, the rotation preventing member 21 comprises a metal staple.

The assembly process of the drug delivery device 1 according to the sixth embodiment is similar to the assembly process discussed with respect to the first embodiment. It differs from the assembly process of the first embodiment only in that the rotation preventing member 21 is engaged to the adjusting member 9 while the external member 17 is still engaged with the controlling feature 16, as shown in FIG. 11.

Figure 12:
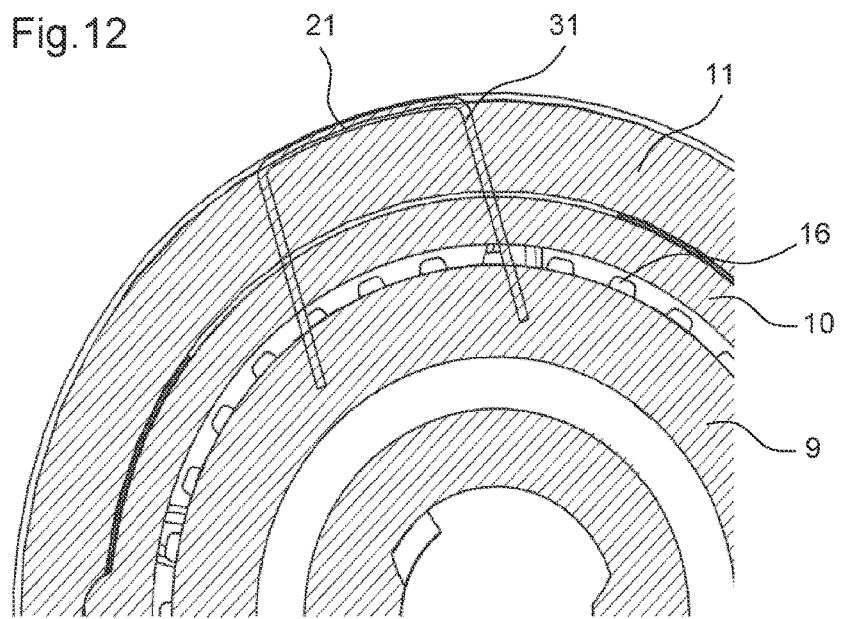
FIG. 12 shows a cross-sectional view of an engagement of the rotation preventing member shown in FIG. 11 with the adjusting member according to the sixth embodiment of the drive mechanism.
Figure 13:
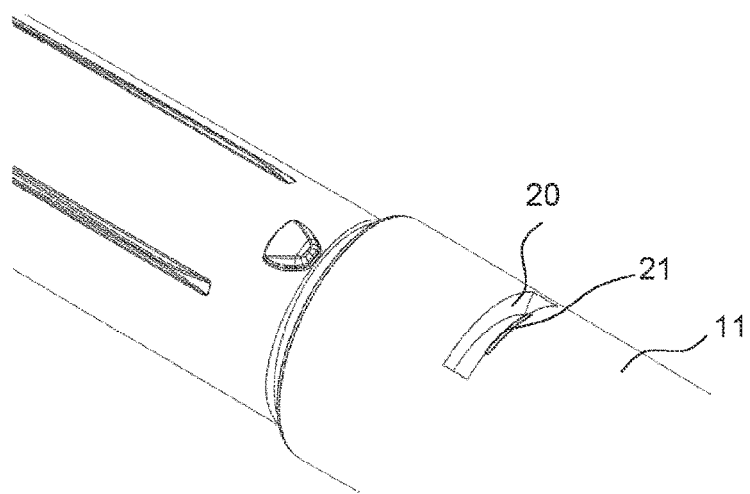
FIG. 13 shows a perspective view of an engagement of the rotation preventing member shown FIGS. 11 and 12 with the adjusting member according to the sixth embodiment of the drive mechanism.

FIGS. 12 and 13 show the drug delivery device 1 wherein the rotation preventing member 21 is engaged with the adjusting member 9. The rotation preventing member 21 is pierced through the body 10 and the adjusting member 9 thereby preventing a further movement of the adjusting member 9 relative to the body 10.

A variation of shape of the rotation preventing member 21 is possible. FIGS. 11 and 12 show the rotation preventing member 21 comprising a metal staple comprising two prongs 31. The staple may alternatively comprise one, three or more prongs 31. The outer surface of the rotation preventing member 21 sits flush with the housing 11 in the second state of the drive mechanism 2, as shown in FIG. 13. Alternatively, the outer surface of the rotation preventing member 21 may be recessed inwards. In an alternate embodiment of the rotation preventing member 21, the rotation preventing member 21 may comprise a flap of metal (not shown) which can be folded over to cover up the opening 20 in the housing 11 once the external member 17 is removed.

In this embodiment the first and the second contact surfaces 25, 27 of the adjusting member 9 and respectively of the body 10 are flat, providing the advantages of a high resolution and a precise axial load on the bung 7. The rotation preventing member 21 as shown in FIG. 1 is optional in this embodiment and may additionally provide for extra locking security and a smooth outer surface of the drug delivery device 1.

Figure 14:
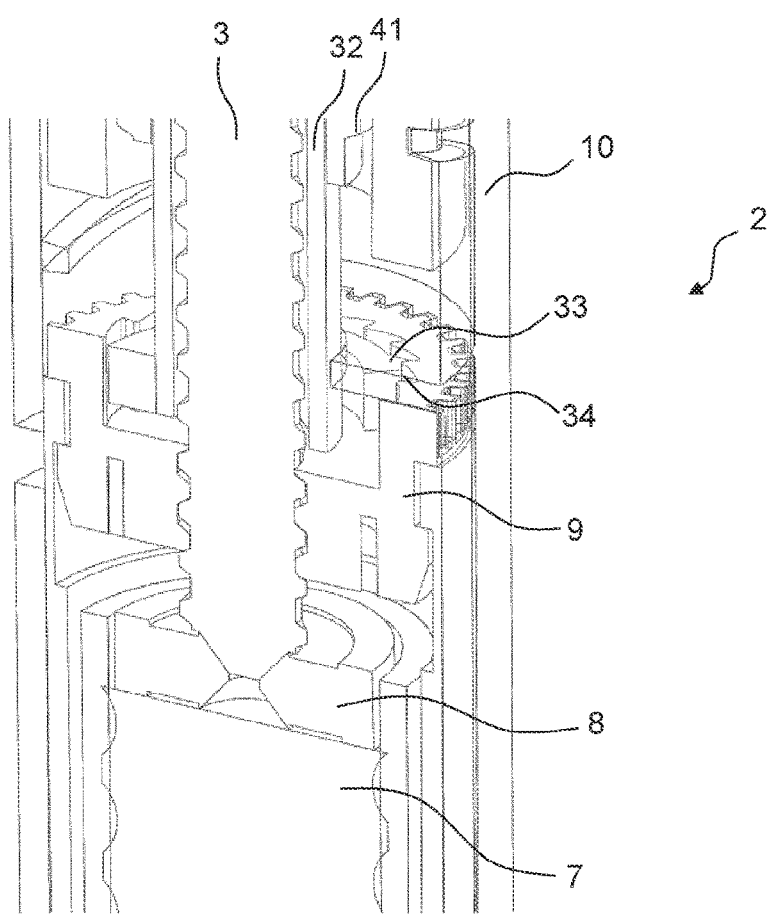
FIG. 14 shows the drive mechanism according to a seventh embodiment.

FIG. 14 shows the drive mechanism 2 according to a seventh embodiment. In the seventh embodiment, a sleeve member 32 is engaged to the adjusting member 9 in the second state of the drive mechanism 2. The sleeve member 32 may comprise a lead screw sleeve. The sleeve member 32 comprises a first locking member 33 at its distal end. Further, the adjusting member 9 comprises a corresponding second locking member 34. In the second state of the drive mechanism 2, the first locking member 33 of the sleeve member 32 is engaged to the second locking member 34 of the adjusting member 9.

The first locking member 33 of the sleeve member 32 comprises a projection, e.g. a clicker arm. The second locking member 34 of the adjusting member 9 comprises teeth arranged at an inner surface of the adjusting member 9, e.g. ratchet teeth. The first and the second locking member 33, 34 are configured such that they permit a rotation of the sleeve member 32 in a first rotational direction and prevent a rotation of the sleeve member 32 in the second rotational direction relative to the adjusting member 9 when engaged to each other.

An engagement of the first and the second locking member 33, 34 may result in an uneven torque profile when the adjusting member 9 is rotated relative to the sleeve member 32 and the body 10. This makes it difficult to accurately determine when the contact between the bearing 8 and the bung 7 is achieved. To avoid this, the adjusting member 9 may be rotated before the second locking member of the adjusting member 9 is engaged with the first locking member of the sleeve member 32.

Figure 15:
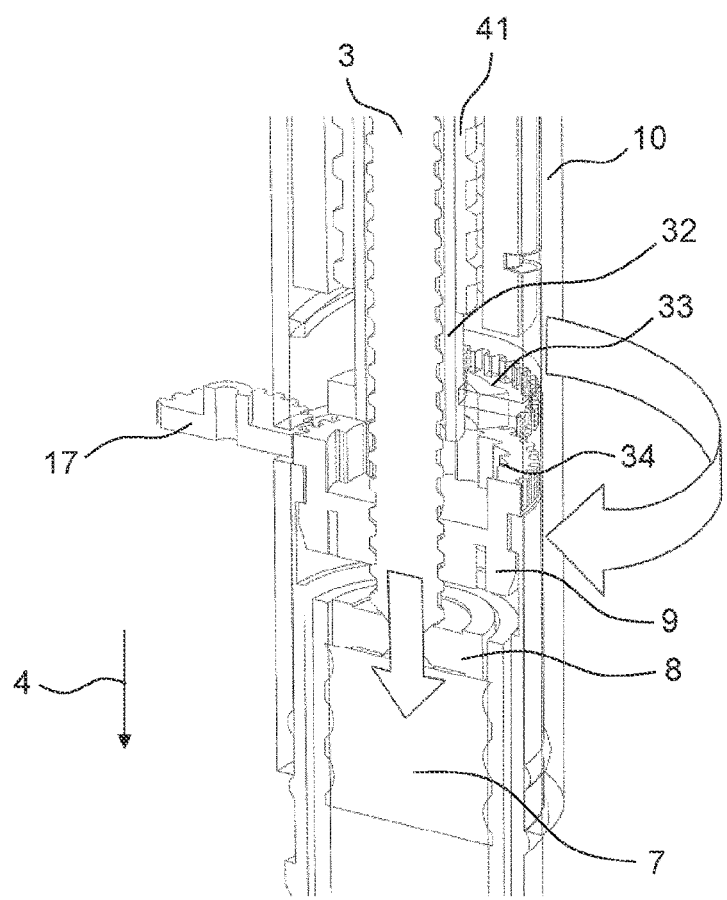
FIG. 15 shows the drive mechanism shown in FIG. 14 in its first state.

Accordingly, the sleeve member 32 is positioned in a proximal position in a distance to the adjusting member 9 in the first state of the drive mechanism 2, as shown in FIG. 15. The adjusting member 9 is then engaged with the external member 17 rotating the adjusting member 9 and thereby moving the piston rod 3 in the distal direction 4. When the bearing 8 contacts the bung 7, the axial load generated in the piston rod 3 will cause the adjusting member 9 to move into contact with the body 10. The external member 17 continues to rotate until the torque has reached the predetermined level indicating that the desired compressive load has been applied to the bung 7. The adjusting member 9 can now be locked in its position relative to the body 10 using any of the techniques described with respect to the first to sixth embodiments.

Figure 16:
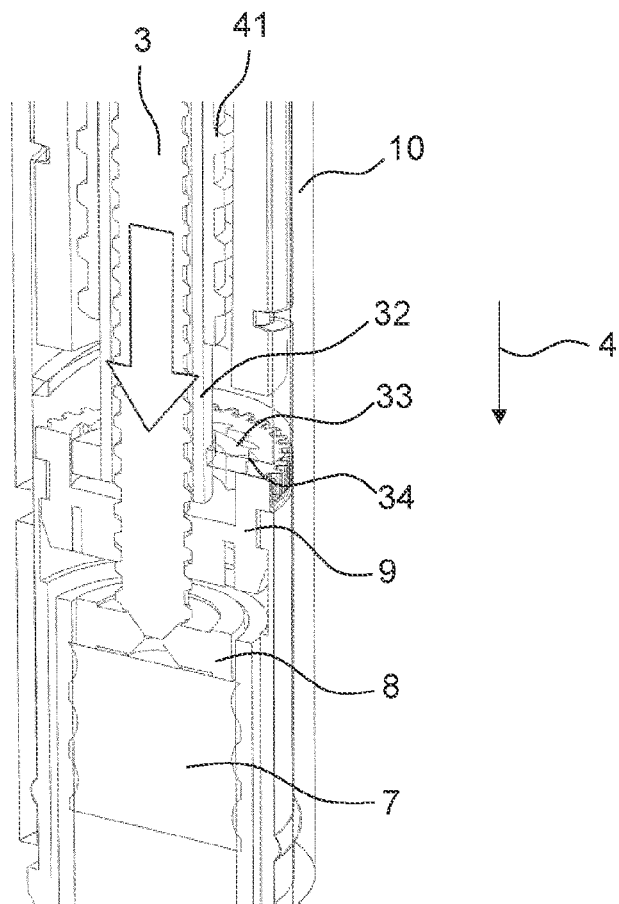
FIG. 16 shows the drive mechanism shown in FIG. 14 in its second state.

In the next assembly step, the sleeve member 32 is moved axially in a distal direction 4 such that the first locking member 33 of the sleeve member 32 engages with the second locking member 34 of the adjusting member 9 as shown in FIG. 16.

If the sleeve member 32 is not present in the first state, an assembly tool may be configured to prevent a purely rotational movement of the piston rod 3 relative to the body 10 when the adjusting member 9 is rotated.

The drive mechanism 2 according to a seventh embodiment further comprises a dial screw 41. During dispense, the dial screw 41 moves helically and the sleeve member 32 moves rotationally. The sleeve member 32 is rotationally constrained to the piston rod 3. The piston rod 3 is threadedly engaged to the adjusting member 9. Rotating the sleeve member 32 therefore causes the piston rod 3 to travel helically during dispense.

Figure 17:
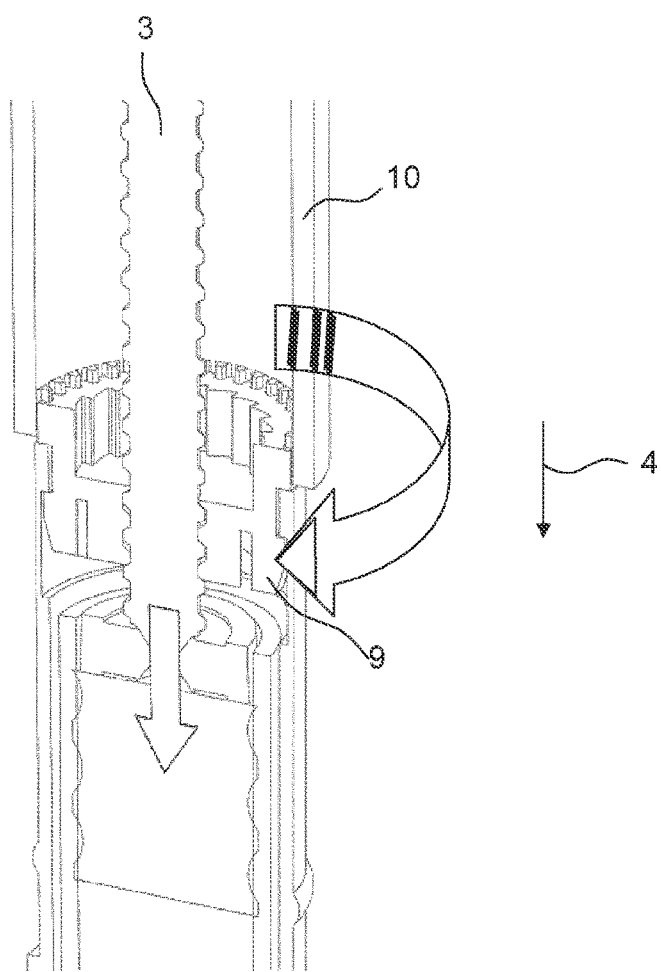
FIG. 17 shows the drive mechanism according to the seventh embodiment when an alternative assembly tool is used.

FIG. 17 shows the drive mechanism 2 when an alternative assembly tool (not shown) is used. The alternative assembly tool drives the piston rod 3 axially in the distal direction 4, resulting in a rotation of the adjusting member 9 relative to the piston rod 3 and, thus, relative to the body 10. The use of the alternative assembly tool can be combined with any of the first to seventh embodiments of the drive mechanism 2.

Figure 18:
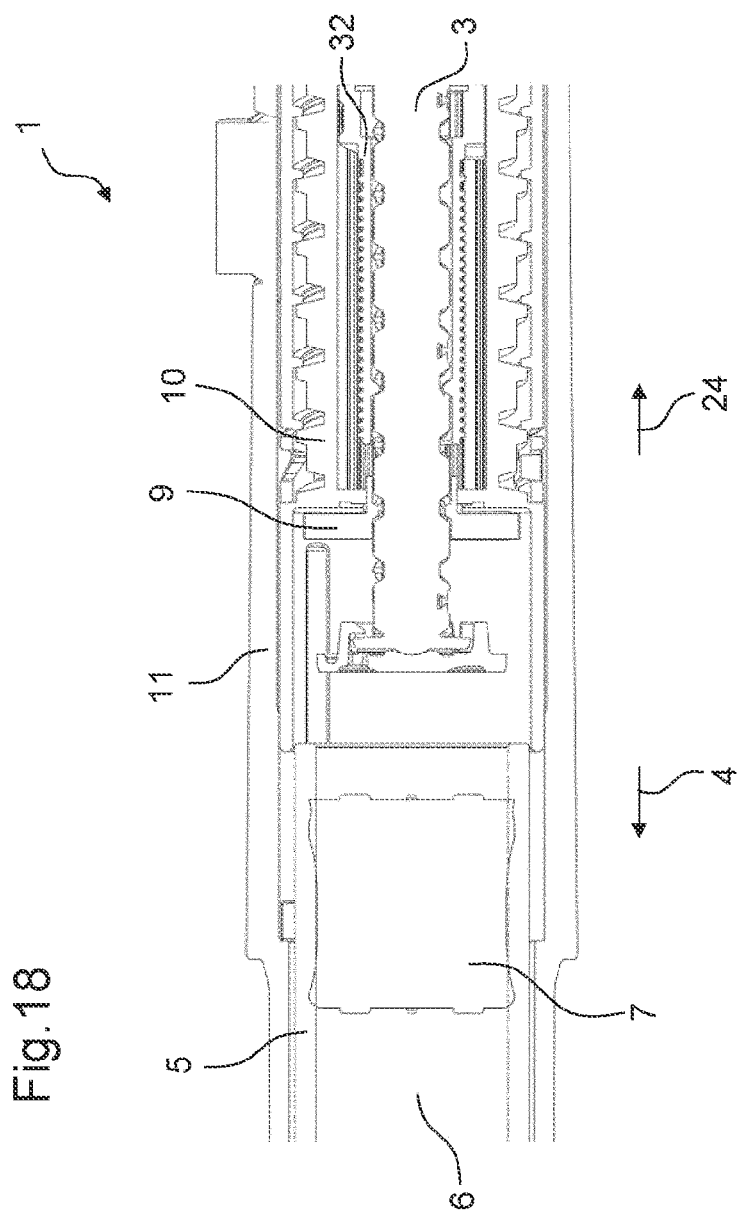
FIG. 18 shows the drug delivery device with the drive mechanism according to an eighth embodiment in a first stage of the assembly process.
Figure 19:
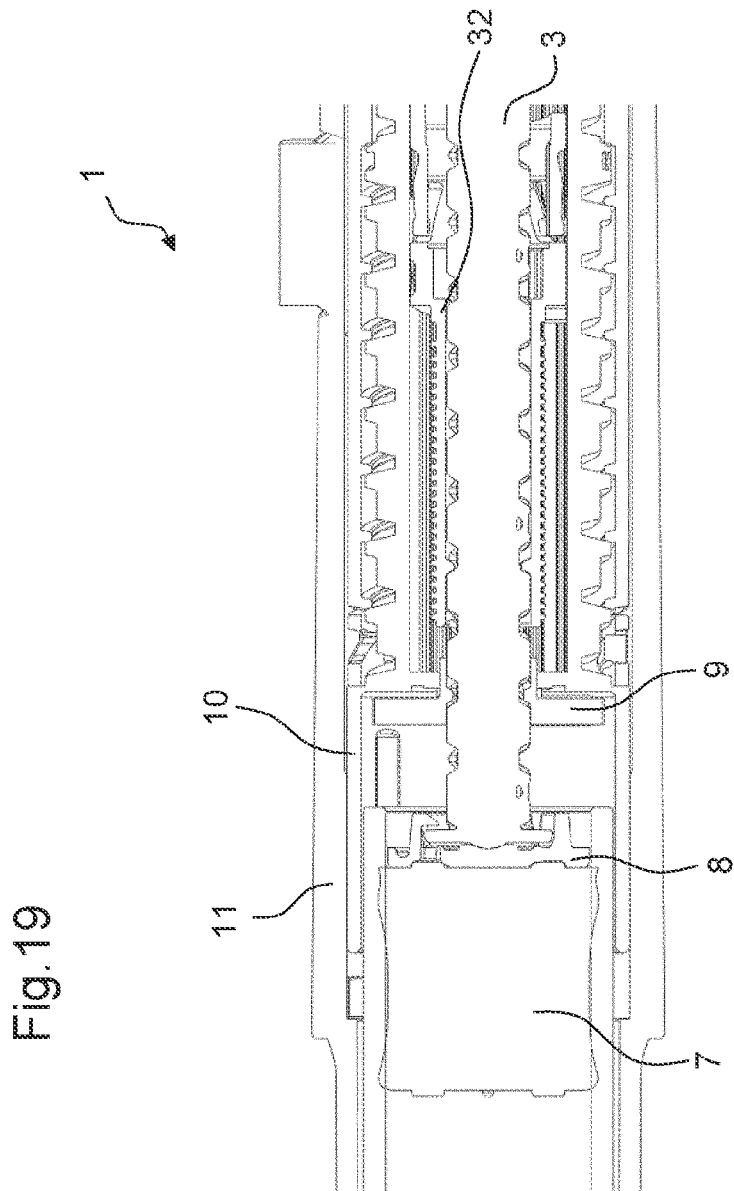
FIG. 19 shows a second stage of the assembly process of the drug delivery device with the drive mechanism according to the eighth embodiment.
Figure 20:
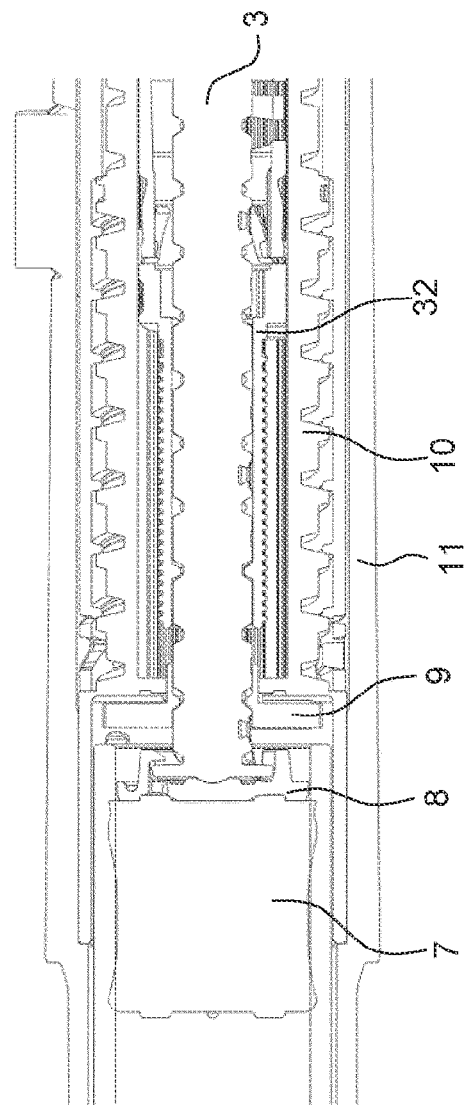
FIG. 20 shows a third stage of the assembly process of the drug delivery device with the drive mechanism according to the eighth embodiment.

FIGS. 18 to 20 show the assembly process of the drug delivery device 1 according to an eighth embodiment.

In the eighth embodiment, the adjusting member 9 is enabled to rotate freely relative to the body 10 when a load is applied by the piston rod 3 on the adjusting member 9. The adjusting members 9 according to the second and the third embodiment are self locking, i.e. the adjusting members 9 according to the second and the third embodiment are prevented from rotating relative to the body 10 when a load is applied by the piston rod 3 on the adjusting member 9. Further, the adjusting members 9 according to the first, the fourth, the fifth, the sixth and the seventh embodiment may be configured either to be enabled to rotate freely relative to the body 10 when a load is applied by the piston rod 3 on the adjusting member 9 or may be configured to be prevented from rotating relative to the body 10 when a load is applied by the piston rod 3 on the adjusting member 9.

FIG. 18 shows the drug delivery device 1 according to the eighth embodiment in a first stage of the assembly process. The body 10, the piston rod 3, the adjusting member 9 and the sleeve member 32 are assembled together and form a sub-assembly. Moreover, a last dose member and a drive member may also be assembled to the sub-assembly. The piston rod 3 is threadedly engaged with the adjusting member 9. In the first stage, the piston rod 3 is positioned such that the piston rod 3 makes contact with the bung 7 of the cartridge 6 in a later assembly stage.

The sub-assembly is then arranged inside the housing 11 which is engaged with the cartridge holder 5 containing the cartridge 6 with the bung 7.

The adjusting member 9 is configured such that it is enabled to rotate relative to the body 10 even if the piston rod 3 applies a load onto the adjusting member 9 in the proximal direction 24.

FIG. 19 shows a second stage of the assembly process of the drug delivery device 1 according to the eighth embodiment. The sub-assembly is moved axially in the distal direction 4 until the bearing 8 of the piston rod 3 abuts the bung 7.

Thereby, the third stage of the assembly process is initiated. FIG. 20 shows the drug delivery device 1 in the third stage of the assembly process.

In the third stage of the assembly process, a further movement of the piston rod 3 in the distal direction 4 is prevented by the abutment of the piston rod 3 and the bung 7. The drive member causes the piston rod 3 to rotate, i.e. the drive member is fixed in rotation relative to the body 10 and is being pushed in axially in the distal direction 4. Further, the drive member is threaded to the piston rod 3, so it causes the piston rod 3 to rotate. Further, the rotation of the piston rod 3 causes the adjusting member 9 to rotate relative to the body 10.

In the first to seventh embodiments, the adjusting member 9 may be configured to self-lock when an axial load is applied to the adjusting member 9 by the piston rod 3. However, in the eighth embodiment, the adjusting member 9 is required to rotate when a load is applied to the piston rod 3, therefore it is not possible to rely on friction against the body 10 to lock the adjusting member 9. The locking techniques discussed above which do not rely on friction between the adjusting member 9 and the body 10 may also be applied to the eighth embodiment, e.g. locking by adhesive or by welding.

Figure 21:
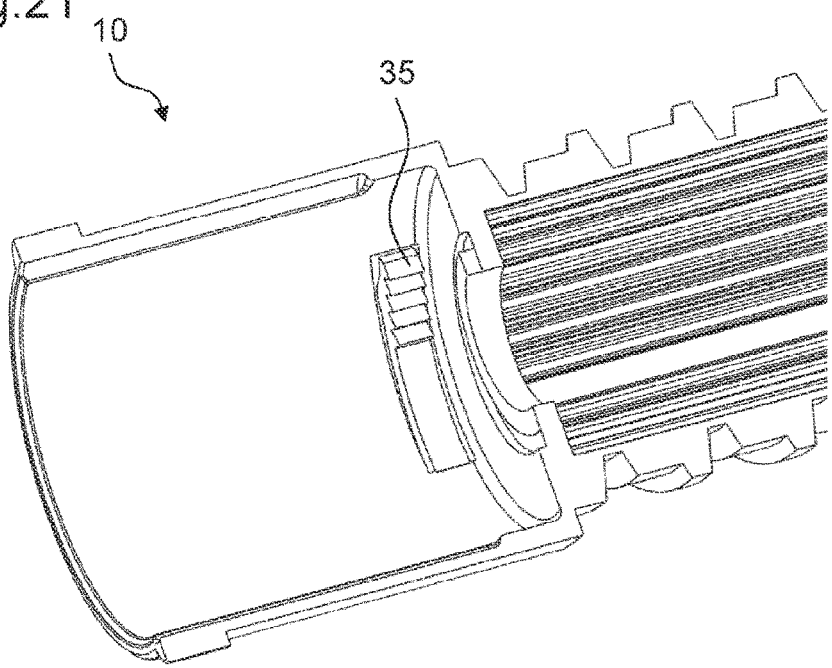
FIG. 21 shows the body according to the ninth embodiment of the drive mechanism.
Figure 22:
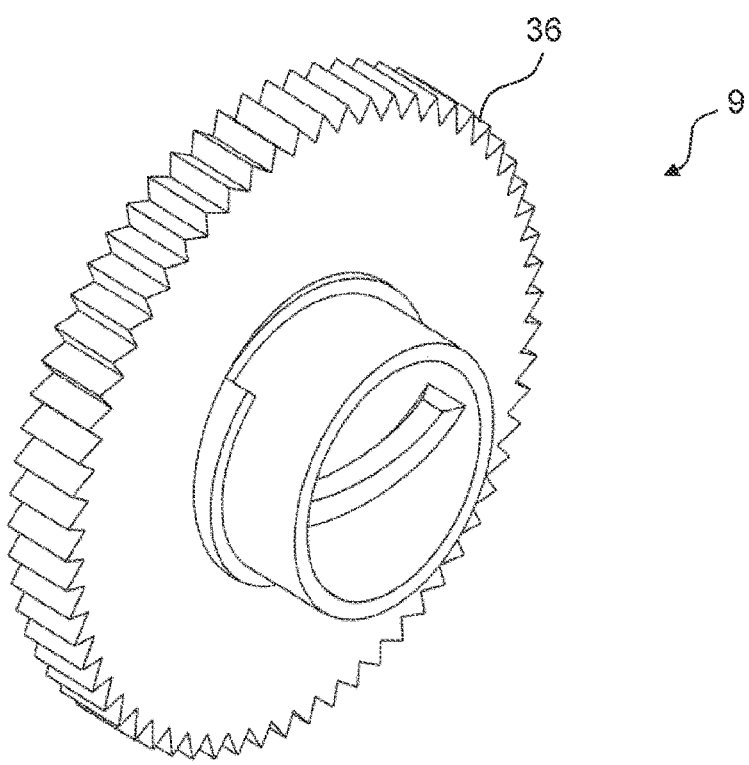
FIG. 22 shows a perspective view of the adjusting member according to the ninth embodiment of the drive mechanism.

FIG. 21 shows a cross-sectional perspective view of the body 10 according to a ninth embodiment. FIG. 22 shows a perspective view of the adjusting member 9 according to the ninth embodiment. The ninth embodiment differs from the eighth embodiment only in respect to the fixing of the adjusting member 9 in the last step of the assembly process.

The body 10 comprises a first engagement feature 35 arranged at its inner surface. The first engagement feature 35 comprises a locking arm. The first engagement feature 35 comprises teeth. The first engagement feature 35 of the body 10 is not engaged with the adjusting member 9 in the first state of the drive mechanism 2.

Moreover, the adjusting member 9 comprises second engagement feature 36. The second engagement feature 36 comprises teeth arranged at the periphery of the adjusting member 9.

Figure 23:
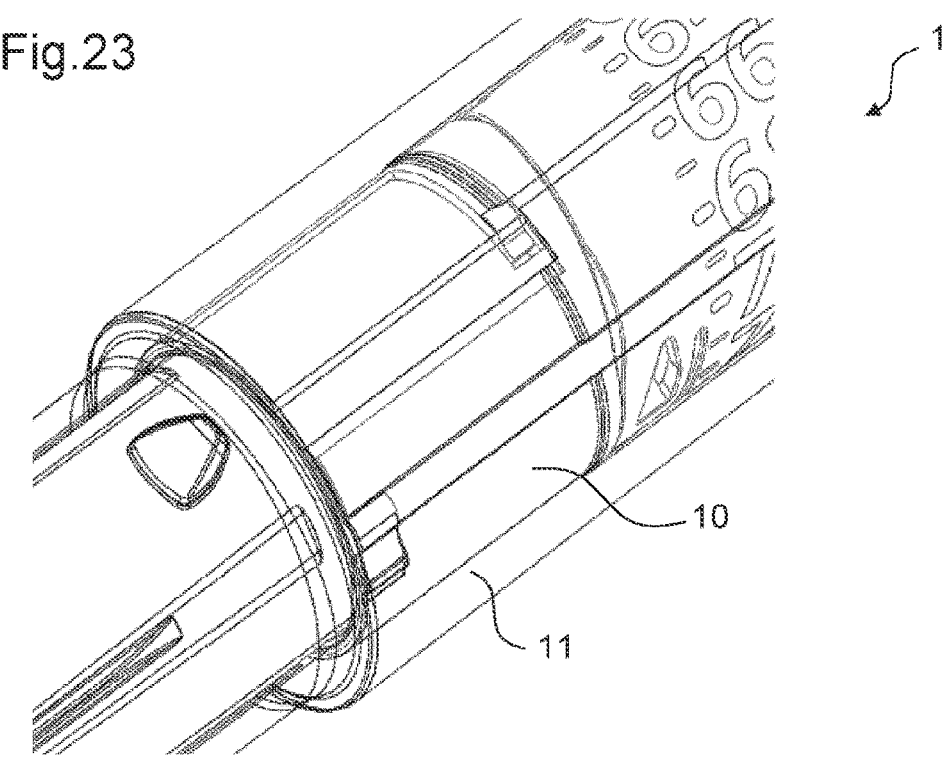
FIG. 23 shows a perspective view of the drug delivery device according to the ninth embodiment in the first state of the drive mechanism.
Figure 24:
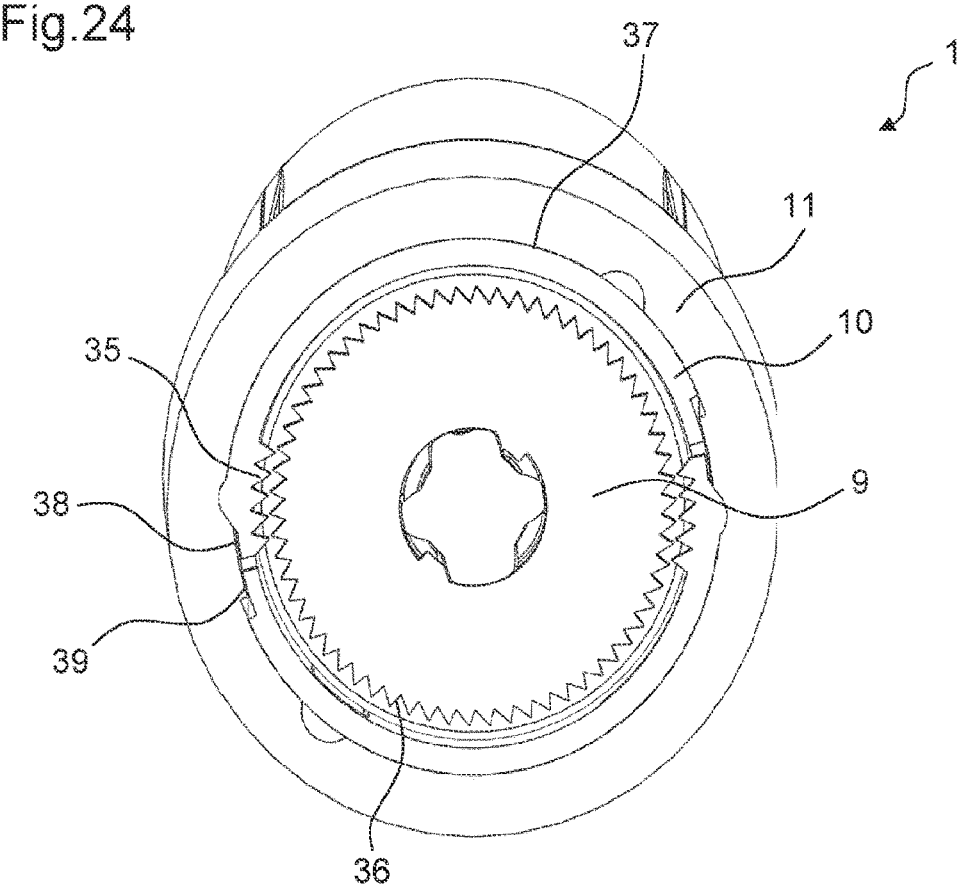
FIG. 24 shows a cross-sectional view of the drug delivery device according to the ninth embodiment in the first state of the drive mechanism.

FIGS. 23 and 24 show the drug delivery device 1 according to the ninth embodiment in the first state of the drive mechanism 2.

In the ninth embodiment, the body 10 is configured such that the body 10 can be rotated relative to the housing 11.

After the adjustment of the axial position of the piston rod 3 has been completed, the body 10 is rotated relative to the housing 11. The body 10 has a non-circular outer diameter 37. The housing 11 has a non-circular inner surface 38 comprising a ramp member 39. Thereby, due to the rotation of the body 10 relative to the housing 11, the first engagement feature 35 of the body 10 is forced inwards by the ramp member 39 of the housing 11. In the second state of the drive mechanism 2, the first engagement feature 35 of the body 10 engages with the second engagement feature 36 of the adjusting member 9.

When the first and the second engagement feature 35, 36 are engaged with each other a further rotation of the adjusting member 9 relative to the body 10 is prevented. The adjusting member 9 must rest in one of a number of discrete positions defined by the meshing of the teeth on the adjusting member 9 with the teeth on the first engagement feature 35 for the first and the second engagement feature 35, 36 to engage with each other. Accordingly, there is a maximum accuracy that can be achieved by this method, defined by the number of teeth.

Figure 25:
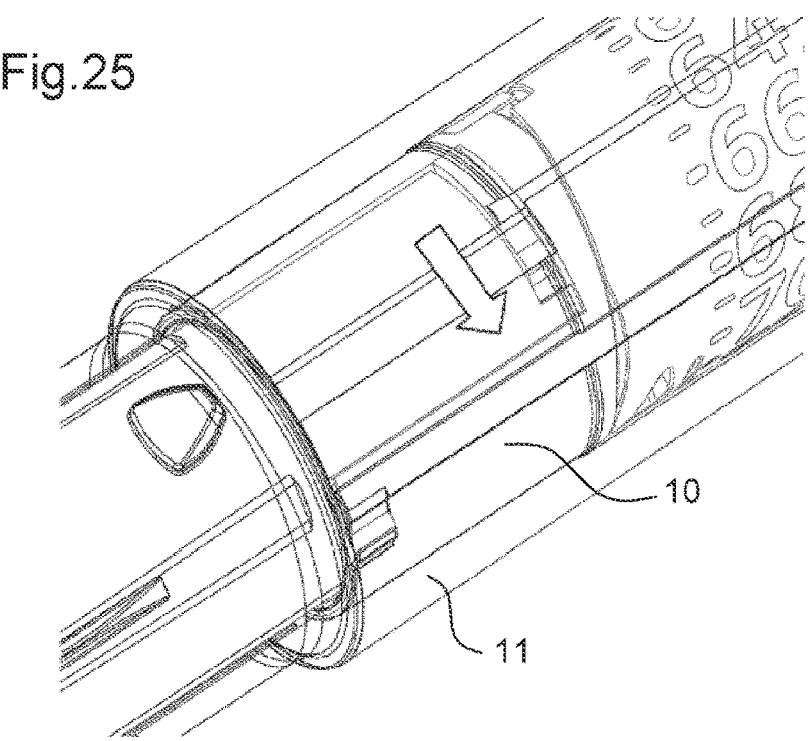
FIG. 25 shows a perspective view of the drug delivery device according to the ninth embodiment in the second state of the drive mechanism.
Figure 26:
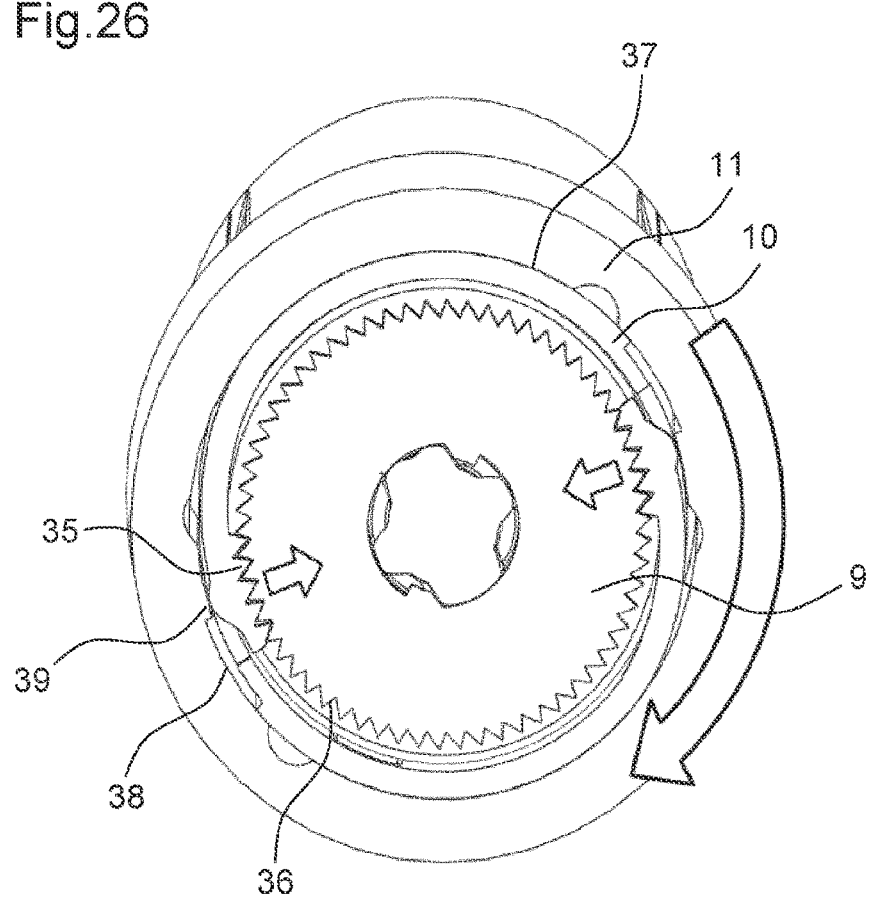
FIG. 26 shows a cross-sectional view of the drug delivery device according to the ninth embodiment in the second state of the drive mechanism.

FIGS. 25 and 26 show the drug delivery device 1 according to the ninth embodiment in the second state of the drive mechanism 2.

Figure 27:
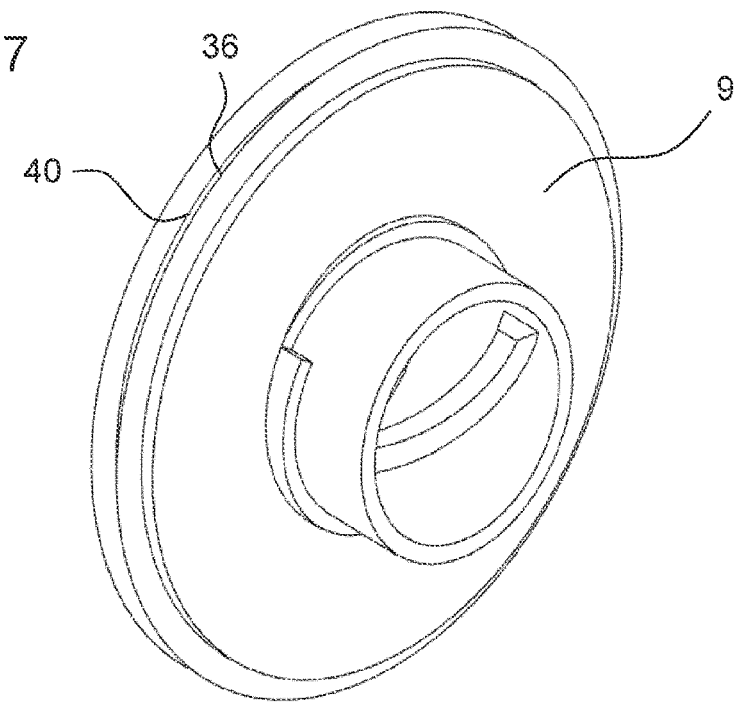
FIG. 27 shows the adjusting member according to a tenth embodiment in a perspective view.

FIG. 27 shows the adjusting member 9 according to a tenth embodiment in a perspective view.

Figure 28:
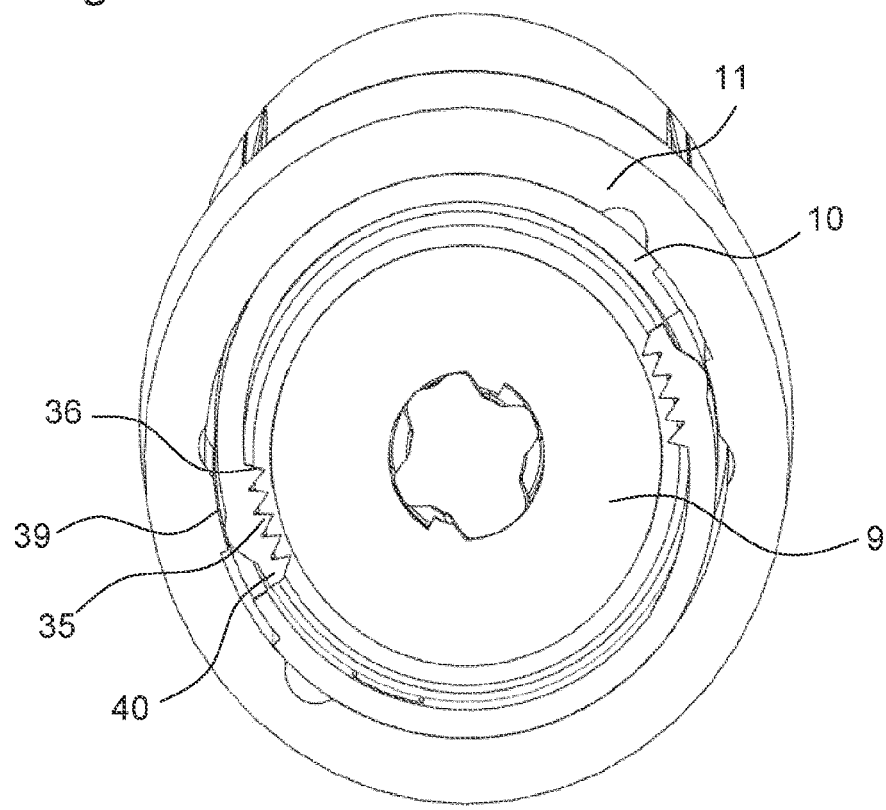
FIG. 28 shows a cross-sectional view of the drug delivery device according to the tenth embodiment in the second state of the drive mechanism.

FIG. 28 shows the drug delivery device 1 according to the tenth embodiment in the second state of the drive mechanism 2.

In the tenth embodiment, the second engagement feature 36 comprises a fragile surface 40 that is configured to be crushed when the first engagement feature 35 of the body 10 engages with the second engagement feature 36. The fragile surface 40 is formed by thin rings that are arranged around the circumference of the adjusting member 9. When the first engagement feature 35 of the body 10 is forced inwards by the ramp member 39 of the housing 11, the first engagement feature 35 crushes the fragile surface 40 and locks the adjusting member 9 in its rotational position relative to the body 10. This allows the adjusting member 9 to be positioned at any rotary position not limited by the need for the first engagement feature 35 to engage with corresponding teeth on the adjusting member 9.

According to an eleventh embodiment, the amount of adjustment in the axial position of the piston rod 3 is determined by a measurement of the positions of the bearing 8 and the bung 7. The sub-assembly is fully assembled as described with respect to the eighth embodiment and the position of the bearing 8 is measured relative to a stop face on the body 10. The cartridge 6 is assembled into the housing 11 and the position of the bung 7 is measured relative to the stop face. A preload force can be applied to the bung 7 at this stage if desired.

With the positions of the bung 7 and the bearing 8 known, the adjusting member 9 can be rotated through a known angle to eliminate the gap between the bung 7 and the bearing 8. A benefit of this concept is that it does not rely on measuring a very small torque to accurately position the piston rod 3. Another benefit is that it may also be possible to rotate the adjusting member 9 by inserting an alternative embodiment of the external member 17 axially into the body 10, rather than via an external member 17 inserted from the side. This would slightly simplify the assembly process by allowing all assembly head movements to be aligned with the longitudinal axis 26 of the drive mechanism 2.

After the assembly is completed, the adjusting member 9 is locked in its position using one of the first to tenth embodiment described above.

The invention claimed is:

1. A drive mechanism for a drug delivery device, the drive mechanism comprising:
   a piston rod;
   an adjusting member; and
   a rotation preventing member,
   wherein the drive mechanism has a first state in which the drive mechanism is operable to perform a priming operation and a second state in which the drive mechanism is operable to perform a dose setting operation and a dose dispensing operation,
   wherein the adjusting member is rotatable relative to a body of the drug delivery device in the first state of the drive mechanism and is configured to be prevented from rotating relative to the body in the second state of the drive mechanism,
   wherein the adjusting member is configured to adjust an axial position of the piston rod in the first state of the drive mechanism,
   wherein the piston rod is configured to be moved in a distal direction when the drive mechanism is operated in its first state, and wherein the piston rod is moveable relative to the adjusting member in the second state of the drive mechanism,
   wherein the adjusting member is configured to constrain a movement of the piston rod in the second state of the drive mechanism such that the piston rod is permitted only to carry out a concurrent axial and rotational movement relative to the adjusting member, and
   wherein the rotation preventing member is configured to be engaged with the adjusting member in the second state of the drive mechanism, thereby preventing the adjusting member from rotating relative to the body.

2. The drive mechanism according to claim 1, wherein the adjusting member is configured such that rotation of an external member is converted into rotation of the adjusting member.

3. The drive mechanism according to claim 2, wherein the adjusting member is configured to be engaged with the external member in the first state of the drive mechanism.

4. The drive mechanism according to claim 1,
   wherein the adjusting member comprises a first contact surface, and
   wherein, in the second state of the drive mechanism, the first contact surface of the adjusting member abuts the body, thereby preventing the adjusting member from rotating relative to the body.

5. The drive mechanism according to claim 4, wherein the first contact surface is configured such that a frictional engagement between the first contact surface and the body prevents the adjusting member from rotating relative to the body in the second state of the drive mechanism.

6. The drive mechanism according to claim 4, wherein, in the second state of the drive mechanism, a force in a proximal direction is exerted onto the adjusting member thereby bringing the first contact surface of the adjustment member in abutment with the body.

7. The drive mechanism according to claim 4, wherein the first contact surface comprises locking features that are configured to engage with the body when the first contact surface abuts the body in the second state of the drive mechanism, thereby preventing the adjusting member from rotating relative to the body.

8. The drive mechanism according to claim 1,
   wherein an adhesive prevents the adjusting member from rotating relative to the body in the second state of the drive mechanism.

9. The drive mechanism according to claim 1,
   wherein the adjusting member comprises a fixing feature, and
   wherein the fixing feature is configured to engage with the body of the drug delivery device such that the adjusting member is either moveable in an axial direction relative to the body only by a small predetermined distance or prevented from moving in the axial direction relative to the body.

10. The drive mechanism according to claim 1, wherein the adjusting member is welded to the body in the second state of the drive mechanism.

11. A drive mechanism for a drug delivery device, the drive mechanism comprising:
    a piston rod; and
    an adjusting member,
    wherein the adjusting member is rotatable relative to a body of the drug delivery device in a first state of the drive mechanism and is configured to be prevented from rotating relative to the body in a second state of the drive mechanism,
    wherein the drive mechanism has a first state in which the drive mechanism is operable to perform a priming operation and a second state in which the drive mechanism is operable to perform a dose setting operation and a dose dispensing operation,
    wherein the adjusting member is configured to adjust an axial position of the piston rod in the first state of the drive mechanism, wherein the piston rod is configured to be moved in a distal direction when the drive mechanism is operated in its first state, and wherein the piston rod is moveable relative to the adjusting member in the second state of the drive mechanism,
    wherein the adjusting member is configured to constrain a movement of the piston rod in the second state of the drive mechanism such that the piston rod is permitted only to carry out a concurrent axial and rotational movement relative to the adjusting member,
    wherein the adjusting member comprises a first contact surface, and
    wherein, in the second state of the drive mechanism, the first contact surface abuts the body, thereby preventing the adjusting member from rotating relative to the body.

12. A drive mechanism for a drug delivery device, the drive mechanism comprising:
    a piston rod; and
    an adjusting member,
    wherein the adjusting member is rotatable relative to a body of the drug delivery device in a first state of the drive mechanism and is configured to be prevented from rotating relative to the body in a second state of the drive mechanism,
    wherein the adjusting member is configured to adjust an axial position of the piston rod in the first state of the drive mechanism, wherein the piston rod is configured to be moved in a distal direction when the drive mechanism is operated in its first state, and wherein the piston rod is moveable relative to the adjusting member in the second state of the drive mechanism, and
    wherein an adhesive prevents the adjusting member from rotating relative to the body in the second state of the drive mechanism or the adjusting member is welded to the body in the second state of the drive mechanism.

13. A drive mechanism for a drug delivery device, the drive mechanism comprising:
a piston rod; and
an adjusting member,
wherein the drive mechanism has a first state in which the drive mechanism is operable to perform a priming operation and a second state in which the drive mechanism is operable to perform a dose setting operation and a dose dispensing operation,
wherein the adjusting member is rotatable relative to a body of the drug delivery device in the first state of the drive mechanism and is configured to be prevented from rotating relative to the body in the second state of the drive mechanism,
wherein the adjusting member is configured to adjust an axial position of the piston rod in the first state of the drive mechanism, wherein the piston rod is configured to be moved in a distal direction when the drive mechanism is operated in its first state, and wherein the piston rod is moveable relative to the adjusting member in the second state of the drive mechanism,
wherein the adjusting member is configured to constrain a movement of the piston rod in the second state of the drive mechanism such that the piston rod is permitted only to carry out a concurrent axial and rotational movement relative to the adjusting member,
wherein the adjusting member comprises a fixing feature, and
wherein the fixing feature is configured to engage with the body of the drug delivery device such that the adjusting member is either moveable in an axial direction relative to the body only by a small predetermined distance or prevented from moving in the axial direction relative to the body.

* * * * *